United States Patent
Yokoyama et al.

(10) Patent No.: US 10,096,779 B2
(45) Date of Patent: Oct. 9, 2018

(54) PYRIMIDINE DERIVATIVES AND ORGANIC ELECTROLUMINESCENT DEVICES

(71) Applicant: HODOGAYA CHEMICAL CO., LTD., Tokyo (JP)

(72) Inventors: Norimasa Yokoyama, Tokyo (JP); Naoaki Kabasawa, Tokyo (JP); Shuichi Hayashi, Tokyo (JP); Jeong-Soo Kim, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/890,270

(22) PCT Filed: May 15, 2014

(86) PCT No.: PCT/JP2014/062932
§ 371 (c)(1),
(2) Date: Nov. 10, 2015

(87) PCT Pub. No.: WO2014/188947
PCT Pub. Date: Nov. 27, 2014

(65) Prior Publication Data
US 2016/0087215 A1 Mar. 24, 2016

(30) Foreign Application Priority Data
May 20, 2013 (JP) .................. 2013-105786

(51) Int. Cl.
*H01L 51/54* (2006.01)
*C09K 11/06* (2006.01)
*H01L 51/00* (2006.01)
*C07D 471/04* (2006.01)
*H01L 51/50* (2006.01)

(52) U.S. Cl.
CPC ........ *H01L 51/0052* (2013.01); *C07D 471/04* (2013.01); *H01L 51/0054* (2013.01); *H01L 51/0067* (2013.01); *H01L 51/0072* (2013.01); *H01L 51/5072* (2013.01);
(Continued)

(58) Field of Classification Search
CPC .. C07D 239/00; C07D 239/02; C07D 239/04; H01L 51/0032; H01L 51/005; H01L 51/0051; H01L 51/0052; H01L 51/0054; H01L 51/0058; H01L 51/0062; H01L 51/0067; H01L 51/0071; H01L 51/0072; H01L 51/50; H01L 51/5012; H01L 51/5016; H01L 51/5048; H01L 51/5072; H01L 51/5088; H01L 51/5092; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| 5,639,914 A | 6/1997 | Tomiyama et al. |
| 5,707,747 A | 1/1998 | Tomiyama et al. |

(Continued)

FOREIGN PATENT DOCUMENTS

| JP | 8-48656 | 2/1996 |
| JP | 2734341 | 1/1998 |

(Continued)

OTHER PUBLICATIONS

Fukagawa et al. Adv. Mater. 2010, 22, 4775-4778. Date of web publication: Aug. 27, 2010.*
(Continued)

*Primary Examiner* — Andrew K Bohaty
(74) *Attorney, Agent, or Firm* — Greenblum & Bernstein, P.L.C.

(57) ABSTRACT

Pyrimidine derivatives of the present invention are represented by the following general formula (1),

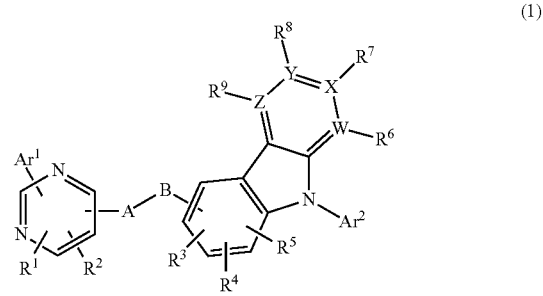

wherein W, X, Y and Z are carbon atoms or nitrogen atoms under the condition that only any one is a nitrogen atom to which none of the groups $R^6$ to $R^9$ are bonded, A and B are single bonds, divalent aromatic hydrocarbon groups or divalent aromatic heterocyclic groups, $Ar^1$ and $Ar^2$ are monovalent aromatic hydrocarbon groups or monovalent aromatic heterocyclic groups, and $R^1$ to $R^9$ are hydrogen atoms, deuterium atoms, fluorine atoms, chlorine atoms, cyano groups, alkyl groups having 1 to 6 carbon atoms, monovalent aromatic hydrocarbon groups or monovalent aromatic heterocyclic groups. The compound excels in electron injection/transporting capability, features high hole-blocking power and high stability in the form of a thin film, and can be favorably used as a material for producing highly efficient and durable organic EL devices.

7 Claims, 2 Drawing Sheets

(52) U.S. Cl.
CPC ...... *H01L 51/5012* (2013.01); *H01L 51/5092* (2013.01); *H01L 51/5096* (2013.01)

(56) References Cited

U.S. PATENT DOCUMENTS

| | | | |
|---|---|---|---|
| 5,792,557 | A | 8/1998 | Nakaya et al. |
| 5,869,199 | A | 2/1999 | Kido |
| 2003/0165715 | A1 | 9/2003 | Yoon et al. |
| 2004/0086745 | A1* | 5/2004 | Iwakuma ............ C07D 401/10 428/690 |
| 2011/0121268 | A1 | 5/2011 | Nagao et al. |
| 2011/0156014 | A1 | 6/2011 | Kim et al. |
| 2011/0291081 | A1 | 12/2011 | Inoue et al. |
| 2012/0126690 | A1 | 5/2012 | Ise et al. |
| 2012/0223276 | A1 | 9/2012 | Parham et al. |
| 2012/0319099 | A1 | 12/2012 | Iwakuma et al. |
| 2013/0306959 | A1 | 11/2013 | Ikeda et al. |
| 2014/0084271 | A1 | 3/2014 | Lee et al. |

FOREIGN PATENT DOCUMENTS

| | | |
|---|---|---|
| JP | 3194657 | 6/2001 |
| JP | 2011-91366 | 5/2011 |
| JP | 2012/501091 | 1/2012 |
| JP | 2013/510803 | 3/2013 |
| KR | 10-2011-0105270 | 9/2011 |
| TW | 200904942 | 2/2009 |
| WO | 2003/060956 | 7/2003 |
| WO | 2010/001817 | 1/2010 |
| WO | 2011/108707 | 9/2011 |
| WO | 2012/086170 | 6/2012 |
| WO | 2012/087007 | 6/2012 |
| WO | 2012/105310 | 8/2012 |
| WO | 2012/150826 | 11/2012 |

OTHER PUBLICATIONS

International Search Report issued in PCT Patent Application No. PCT/JP2014/062932, dated Jul. 29, 2014.

Fukagawa et al., "Pyridoindole Derivative as Electron Transporting Host Material for Efficient Deep-blue Phosphorescrent Organic Light-emitting Diodes"; Advanced Materials, vol. 22; 2010; pp. 4775-4778.

Taiwanese Office Action issued in Counterpart Patent Application No. 103117517, dated Nov. 16, 2017.

* cited by examiner

9: CATHODE
8: ELECTRON INJECTION LAYER
7: ELECTRON-TRANSPORTING LAYER
6: HOLE-BLOCKING LAYER
5: LUMINOUS LAYER
4: HOLE-TRANSPORTING LAYER
3: HOLE INJECTION LAYER
2: TRANSPARENT ANODE
1: GLASS SUBSTRATE

PYRIMIDINE DERIVATIVES AND ORGANIC ELECTROLUMINESCENT DEVICES

FIELD OF THE INVENTION

This invention relates to novel pyrimidine derivatives having a pyrimidine ring structure and a pyridoindole ring structure. More specifically, the invention relates to pyrimidine derivatives suited for an organic electroluminescent device (hereinafter abbreviated as organic EL device) that is a spontaneously luminous device that can be favorably used for various kinds of display devices, and to an organic EL device that uses the pyrimidine derivative as a material for constituting organic layers.

BACKGROUND ART

An organic EL device is a spontaneously luminous device which features higher brightness and higher legibility than those of liquid crystal devices enabling vivid display to be attained and has, therefore, been vigorously studied.

In 1987, C. W. Tang et al. of Eastman Kodak Company have developed a device of a layer-laminated structure comprising various kinds of materials to bear individual roles, and have put an organic EL device using organic materials into a practical use. The above organic EL device is constituted by laminating layers of a fluorescent body capable of transporting electrons and of an organic material capable of transporting holes. Upon injecting both electric charges into the layer of the fluorescent body to emit light, the device is capable of attaining a brightness of as high as 1000 cd/m$^2$ or more with a voltage of not higher than 10 V (see, for example, a patent document 1 and a patent document 2).

So far, very many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, however, what is important is how efficiently to hand both electric charges, i.e., holes and electrons, over to the luminous layer. Upon improving the electron injection property, improving the mobility thereof and, therefore, improving the probability of recombination of the holes and the electrons and, further, confining the excitons formed in the luminous layer, it is allowed to attain a high luminous efficiency. Namely, the electron-transporting material plays an important role. Therefore, it has been desired to provide an electron-transporting material that has a high electron injection property, a large electron migration rate, a high hole-blocking property and a large durability against the holes.

As for the life of the device, further, the heat resistance and amorphousness of the material also serve as important factors. The material having small heat resistance is subject to be thermally decomposed even at a low temperature due to the heat generated when the device is driven, and is deteriorated. The material having low amorphousness permits the thin film thereof to be crystallized in short periods of time and, therefore, the device to be deteriorated. Therefore, the material to be used must have large heat resistance and good amorphousness.

Tris(8-hydroxyquinoline)aluminum (hereinafter abbreviated as Alq) which is a representative luminous material has also been generally used as an electron-transporting material having, however, a hole-blocking power which is far from satisfactory.

A method of inserting a hole-blocking layer is one of the measures for preventing the holes from partly passing through the luminous layer to improve the probability of recombination of the electric charge in the luminous layer. As a hole-blocking material, there have heretofore been proposed trizaole derivatives (see, for example, a patent document 3). There have, further, been known a bathocuproin (hereinafter abbreviated as BCP) and a mixed ligand complex of aluminum [aluminum (III) bis(2-methyl-8-quinolinato)-4-phenyl phenolate (hereinafter abbreviated as BAlq).

There has, further, been proposed a 3-(4-biphenylyl)-4-phenyl-5-(4-t-butylphenyl)-1,2,4-triazole (hereinafter abbreviated as TAZ) as a material having excellent hole-blocking power (see, for example, the patent document 3).

The TAZ has a work function of as large as 6.6 eV and a large hole-blocking power, and is used for forming an electron-transporting hole-blocking layer that is laminated on the cathode side of a fluorescent luminous layer or a phosphorescent luminous layer prepared by vacuum evaporation or by coating and, therefore, contributes to improving the efficiency of the organic EL devices.

Because of a serious problem of low electron-transporting capability, however, the TAZ had to be used in combination with an electron-transporting material having a higher electron-transporting capability to fabricate the organic EL devices.

The BCP, on the other hand, has a work function of as large as 6.7 eV and a large hole-blocking power but a glass transition point (Tg) of as low as 83° C. In the form of a thin film, therefore, the BCP lacks stability and still cannot be said to be sufficiently working as the hole-blocking layer.

Either material still lacks stability when it is formed into a film or lacks the function for blocking the holes to a sufficient degree. In order to improve characteristics of the organic EL devices, therefore, it has been desired to provide an organic compound that excels in electron injection/transporting capability and in hole-blocking power, and features high stability in the form of a thin film.

PRIOR ART DOCUMENTS

Patent Documents

Patent document 1: JP-A-8-48656
Patent document 2: Japanese Patent No. 3194657
Patent document 3: Japanese Patent No. 2734341
Patent document 4: WO2003/060956

OUTLINE OF THE INVENTION

Problems that the Invention is to Solve

The object of the present invention is to provide a novel organic compound that excels in electron injection/transporting capability, features a hole-blocking power and a high stability in the form of a thin film, and can be favorably used as a material for producing highly efficient and highly durable organic EL devices.

The other object of the present invention is to provide an organic EL device which features a high efficiency, a low driving voltage and a large durability.

Means for Solving the Problems

To achieve the above object, the present inventors have paid attention to that a nitrogen atom of a pyrimidine ring having affinity to electron is capabile of being coordinated on a metal, and to that a pyridoindole ring structure has excellent heat resistance, and have designed and chemically synthesized a compound that has the pyrimidine ring structure and the pyridoindole ring structure, have prepared various organic EL devices by using the above compound on an experimental basis, have keenly evaluated the properties of the device and, as a result, have completed the present invention.

According to the present invention, there are provided pyrimidine derivatives represented by the following general formula (1),

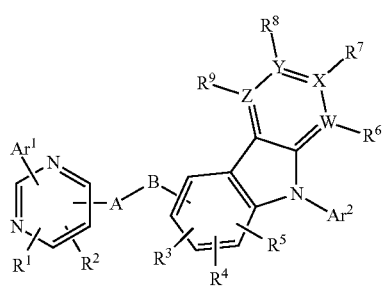

(1)

wherein,
W, X, Y and Z are carbon atoms or nitrogen atoms under the condition that only any one of them is a nitrogen atom to which none of the groups $R^6$ to $R^9$ are bonded,
A and B may be the same or different, and are single bonds, divalent aromatic hydrocarbon groups or divalent aromatic heterocyclic groups and if A and B are both single bonds, the pyrimidine ring and the pyridoindole ring are bonded together via the single bond,
$Ar^1$ and $Ar^2$ may be the same or different, and are monovalent aromatic hydrocarbon groups or monovalent aromatic heterocyclic groups, and
$R^1$ to $R^9$ may be the same or different, and are hydrogen atoms, deuterium atoms, fluorine atoms, chlorine atoms, cyano groups, alkyl groups having 1 to 6 carbon atoms, monovalent aromatic hydrocarbon groups or monovalent aromatic heterocyclic groups.

In the pyrimidine derivatives of the present invention, it is desired that:
(a) In the above general formula (1), A or B is a single bond or a divalent aromatic hydrocarbon group; and
(b) In the above general formula (1), A and B are both single bonds, and the pyrimidine ring and the pyridoindole ring are bonded together via the single bond.

It is desired that the pyrimidine derivatives of the present invention:
(c) Have a molecular structure represented by the following general formula (1-1);

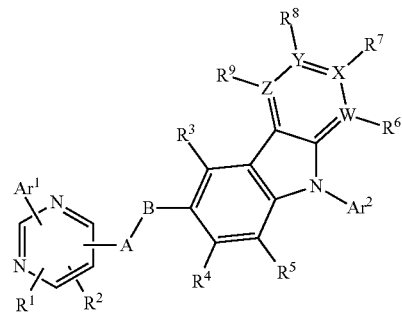

(1-1)

wherein A, B, $Ar^1$, $Ar^2$, $R^1$ to $R^9$, W, X, Y and Z are as defined above;
(d) Have the group A bonded to the fourth position of the pyrimidine ring;
(e) Have the group $Ar^1$ bonded to the second position of the pyrimidine ring;
(f) Have the group A bonded to the second position of the pyrimidine ring; and
(g) Have the group $Ar^1$ bonded to the fourth position of the pyrimidine ring.

According to the present invention, further, there is provided an organic EL device having a pair of electrodes and at least one organic layer held therebetween, wherein the pyrimidine derivative is used as the material for constituting at least one organic layer.

In the organic EL device of the invention, the organic layer formed by using the pyrimidine derivative as a constituent material may be any one of an electron-transporting layer, a hole-blocking layer, a luminous layer or an electron injection layer.

Effects of the Invention

The pyrimidine derivatives of the invention represented by the above general formula (1) are novel compounds having a pyrimidine ring structure and a pyridoindole ring structure, and feature the following properties.
(A) The electrons can be favorably injected.
(B) The electrons migrate at a high rate.
(C) The holes can be blocked favorably.
(D) Remains stable in a thin-film state.
(E) Excellent heat resistance.

Therefore, the organic EL device having an organic layer formed by using, as a constituting material, the pyrimidine derivative having the above properties, feature:
(F) A high luminous efficiency.
(G) A low luminescence start voltage.
(H) A low practical driving voltage.
(I) A high maximum brightness.
(J) A long service life.

For instance, the organic EL device forming the electron injection layer and/or the electron-transporting layer by using the pyrimidine derivative of the invention, features an improved electron transport efficiency from the electron-transporting layer into the luminous layer as compared to the conventional organic EL devices and, therefore, features a high luminous efficiency, a low driving voltage and a large durability.

Further, the organic EL device having a hole-blocking layer formed by using the pyrimidine derivative of the invention features not only excellent hole-blocking power but also excellent electron-transporting capability as compared to the conventional organic EL devices, as well as high stability in the state of a thin film and, therefore, requires a decreased driving voltage yet maintaining a high luminous efficiency and, besides, features an improved resistance against the electric current and an improved maximum brightness.

Further, the pyrimidine derivative of the invention features excellent electron transport capability and a wide band gap and can, therefore, be used as a host material for the luminous layer. By using the pyrimidine derivative of the invention as a luminous layer which, further, carries a fluorescent material or a luminous phosphor called dopant thereon, it is made possible to lower the driving voltage of the organic EL device and to improve the luminous efficiency.

Further, the pyrimidine derivative of the present invention has a higher electron injection capability, a larger mobility, higher hole-blocking power, higher stability against the holes and higher stability in the state of a thin film than those of the conventional electron-transporting materials. Therefore, the organic EL device having the hole-blocking layer formed by using the pyrimidine derivative of the invention is capable of confining the excitons formed in the luminous layer, improving the probability of recombining the holes with the electrons, attaining a high luminous efficiency, lowering the driving voltage and realizing a high durability.

MODES FOR CARRYING OUT THE INVENTION

Figure 1:
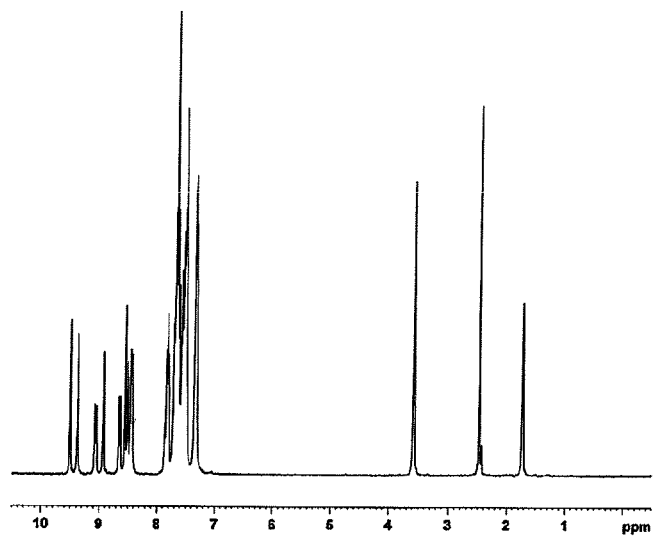
FIG. 1 is a $^1$H-NMR chart of a compound (compound 1) of Example 1.

The novel pyrimidine derivatives of the present invention are represented by the following general formula (1) and their basic skeletons have a pyrimidine ring structure and a pyridoindole ring structure.

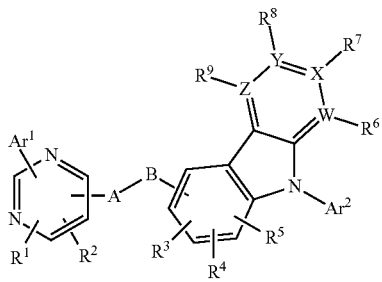

(1)

<W, X, Y, Z>

In the above general formula (1), W, X, Y and Z are atoms in the pyridoindole ring, and are carbon atoms or nitrogen atoms under the condition that only any one of them is a nitrogen atom.

None of the groups $R^6$ to $R^9$ are bonded to the nitrogen atom in the ring. That is, if W is the nitrogen atom, the group $R^6$ is not bonded to W (nitrogen atom) (group $R^6$ is not present). If X is the nitrogen atom, the group $R^7$ is not bonded to X (nitrogen atom) (group $R^7$ is not present). If Y is the nitrogen atom, the group $R^8$ is not bonded to Y (nitrogen atom) (group $R^8$ is not present). If Z is the nitrogen atom, the group $R^9$ is not bonded to Z (nitrogen atom) (group $R^9$ is not present).

In the invention, it is desired that Y or Z is the nitrogen atom and it is more desired that Y is the nitrogen atom.

<A, B>

In the general formula (1), A and B are groups crosslinking the pyrimidine ring to the pyridoindole ring. A and B may be the same or different, and are single bonds, divalent aromatic hydrocarbon groups or divalent aromatic heterocyclic groups.

If A and B are both the single bonds, it means that the pyrimidine ring and the pyridoindole ring are bonded via the single bonds.

The divalent aromatic hydrocarbon group and the divalent aromatic heterocyclic group, either, may have a condensed polycyclic structure.

As the aromatic hydrocarbon ring and the aromatic heterocyclic ring possessed by these groups, there can be exemplified benzene, biphenyl, terphenyl, tetrakisphenyl, naphthalene, anthracene, acenaphthalene, fluorine, phenanthrene, indane, pyrene, pyridine, pyrimidine, triazine, furan, pyran, thiophene, quinolone, isoquinoline, benzofuran, benzothiophene, indoline, carbazole, carboline, benzoxazole, benzthiazole, quinoxaline, benzimidazole, pyrazole, dibenzofuran, dibenzothiophene, naphthylidine, phenathroline and acrydinine.

The above divalent aromatic hydrocarbon group and the divalent aromatic heterocyclic group may, further, have substituents. As the substituents, there can be exemplified the following groups:

Deuterium;

cyano group;

nitro group;

halogen atom such as fluorine atom, chlorine atom, bromine atom or iodine atom;

alkyl group having 1 to 6 carbon atoms, such as methyl group, ethyl group, n-propyl group, isopropyl group, n-butyl group, isobutyl group, tert-butyl group, n-pentyl group, isopentyl group, neopentyl group or n-hexyl group;

alkyloxy group having 1 to 6 carbon atoms, such as methyloxy group, ethyloxy group or propyloxy group;

alkenyl group such as allyl group;

aryloxy group such as phenyloxy group or tolyloxy group;

arylalkyloxy group such as benzyloxy group or phenetyloxy group;

monovalent aromatic hydrocarbon group such as phenyl group, biphenylyl group, terphenylyl group, naphthyl group, anthracenyl group, phenanthryl group, fluorenyl group, indenyl group, pyrenyl group, perylenyl group, fluoranthenyl group, or triphenylenyl group;

monovalent aromatic heterocyclic group such as pyridyl group, thienyl group, furyl group, pyrolyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group or, carbolinyl group;

arylvinyl group such as stylyl group or naphthylvinyl group; and acyl group such as acetyl group or benzoyl group.

The substituents exemplified above may, further, have similar substituents under the condition that they do not break the limitation on the number of the carbon atoms.

Further, though not so much preferred, the substituents exemplified above may form a ring being bonded together via single bond, substituted or unsubstituted methylene group, oxygen atom or sulfur atom.

In the invention, the above A and B are, preferably, single bonds or divalent aromatic hydrocarbon groups (specifically, divalent benzene ring groups or divalent anthracene ring groups).

<$Ar^1$, $Ar^2$>

In the above general formula (1), $Ar^1$ and $Ar^2$ may be the same or different, and are monovalent aromatic hydrocarbon groups or monovalent aromatic heterocyclic groups.

As the monovalent aromatic hydrocarbon group and the monovalent aromatic heterocyclic group, there can be exemplified phenyl group, biphenylyl group, terphenylyl group, tetrakisphenyl group, stylyl group, naphthyl group, anthryl group, acenaphthenyl group, phenanthryl group, fluorenyl group, indenyl group, pyrenyl group, triazyl group, pyridyl group, pyrimidyl group, furyl group, pyrolyl group, thienyl group, quinolyl group, isoquinolyl group, benzofuranyl group, benzothienyl group, indolyl group, carbazolyl group, benzoxazolyl group, benzthiazolyl group, quinoxalyl group, benzimidazolyl group, pyrazolyl group, dibenzofuranyl group, dibenzothienyl group, naphthylydinyl group, phenanthrolynyl group and acrydinyl group.

In the invention, $Ar^1$ is, preferably, among the groups exemplified above, phenyl group, biphenylyl group, naphthyl group, anthryl group, phenanthryl group, fluorenyl group, pyridyl group, pyrimidyl group, quinolyl group or isoquinolyl group and is, more preferably, phenyl group, biphenylyl group, naphtyl group, anthryl group or phenanthryl group.

Further, $Ar^2$ is, preferably, phenyl group, biphenylyl group, naphthyl group, anthryl group, phenanthryl group, fluorenyl group, pyridyl group, pyrimidyl group, quinolyl group or isoquinolyl group and, more preferably, phenyl group, biphenylyl group, naphthyl group, fluorenyl group, pyridyl group or pyrimidyl group.

The above monovalent aromatic hydrocarbon group and the monovalent aromatic heterocyclic group, too, may have a substituent. As the substituent, there can be exemplified the same substituents as those exemplified in the paragraph of the divalent aromatic hydrocarbon groups and the divalent aromatic heterocyclic groups. Like the above-mentioned cases of the divalent aromatic hydrocarbon groups and divalent aromatic heterocyclic groups, these substituents, too, may further have a substituent. Besides, though not so preferable, the substituents may be bonded together to form a ring.

<$R^1$ to $R^9$>

In the general formula (1), further, $R^1$ to $R^9$ may be the same or different, and are hydrogen atoms, deuterium atoms, fluorine atoms, chlorine atoms, cyano groups, alky groups having 1 to 6 carbon atoms, monovalent aromatic hydrocarbon groups, or monovalent aromatic heterocyclic groups.

As the alkyl groups denoted by $R^1$ to $R^9$, there can be exemplified methyl groups, ethyl groups, n-propyl groups, i-propyl groups, n-butyl groups, 2-methylpropyl groups, t-butyl groups, n-pentyl groups, 3-methylbutyl groups, tert-pentyl groups, n-hexyl groups, iso-hexyl groups and tert-hexyl groups.

As the monovalent aromatic hydrocarbon groups and the monovalent aromatic heterocyclic groups, there can be exemplified the same groups as those exemplified for $Ar^1$ and $Ar^2$.

In the invention, as the groups $R^1$ and $R^2$ bonded, specifically, to the pyrimidine ring, there can be exemplified, preferably, hydrogen atoms, deuterium atoms, phenyl groups, biphenylyl groups, naphthyl groups, anthryl groups, phenanthryl groups, fluorenyl groups, pyridyl groups, pyrimidyl groups, quinolyl groups and isoquinolyl groups and, more preferably, hydrogen atoms, phenyl groups, biphenyl groups, naphthyl groups, anthryl groups and phenanthryl groups.

The above-mentioned groups $R^1$ to $R^9$, too, may have a substituent. As the substituent, there can be exemplified the same substituents as those exemplified in the paragraph of divalent aromatic hydrocarbon groups and divalent aromatic heterocyclic groups. Like the above-mentioned cases of the divalent aromatic hydrocarbon groups and divalent aromatic heterocyclic groups, these substituents, too, may further have a substituent. Besides, though not so preferable, the substituents may be bonded together to form a ring.

<Preferred Crosslinked Structures>

It is desired that the pyrimidine derivatives of the invention represented by the above general formula (1) have a crosslinked structure in which the indole ring in the pyridoindole ring structure is bonded at its fifth position to the pyrimidine ring. The pyrimidine derivatives having the above crosslinked structure can be presented by the following general formula (1-1).

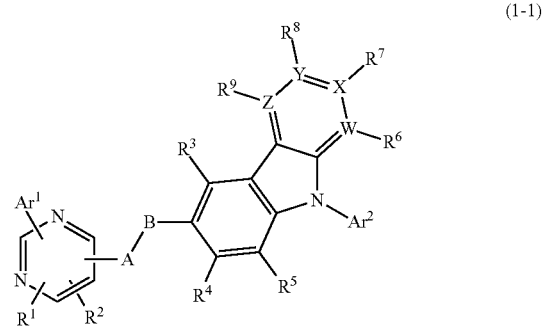

(1-1)

wherein A, B, $Ar^1$, $Ar^2$, $R^1$ to $R^9$, W, X, Y and Z are as defined above.

The pyrimidine derivatives represented by the above general formula (1-1) can be, further, divided into those of the type in which the group A is bonded to the fourth position of the pyrimidine ring and those of the type in which it is bonded to the second position thereof.

The pyrimidine derivatives of the type in which the group A is bonded to the fourth position of the pyrimidine ring are represented by the following general formula (1a-1).

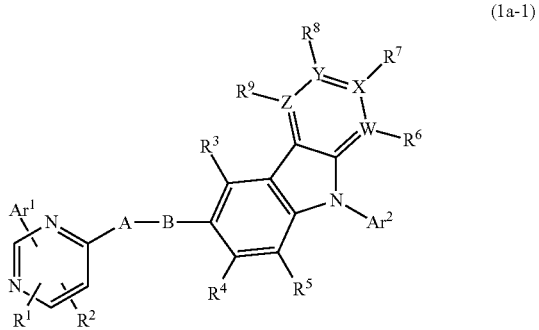

(1a-1)

wherein A, B, Ar$^1$, Ar$^2$, R$^1$ to R$^9$, W, X, Y and Z are as defined above.

In the pyrimidine derivatives of this type, it is desired that the group Ar$^1$ is bonded to the second position of the pyrimidine ring. These compounds are represented by the following general formula (1a-2).

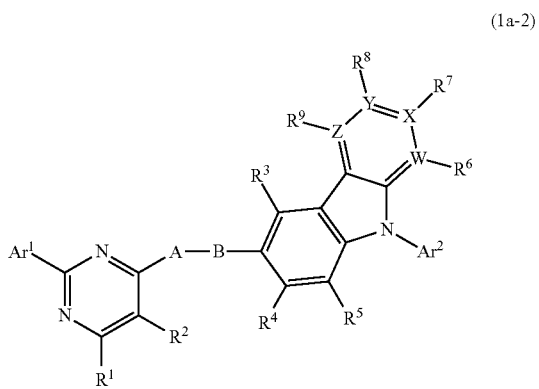

(1a-2)

wherein A, B, Ar$^1$, Ar$^2$, R$^1$ to R$^9$, W, X, Y and Z are as defined above.

Further, the pyrimidine derivatives of the type in which the group A is bonded to the second position of the pyrimidine ring are represented by the following general formula (1b-1).

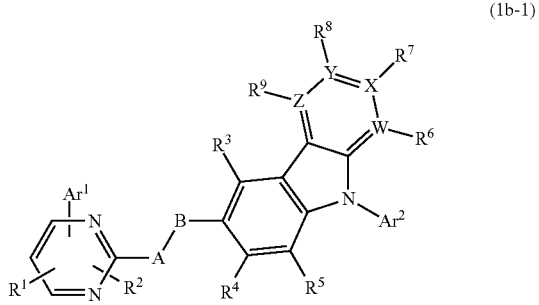

(1b-1)

wherein A, B, Ar$^1$, Ar$^2$, R$^1$ to R$^9$, W, X, Y and Z are as defined above.

In the pyrimidine derivatives of this type, it is desired that the group Ar$^1$ is bonded to the fourth position of the pyrimidine ring. These compounds are represented by the following general formula (1b-2).

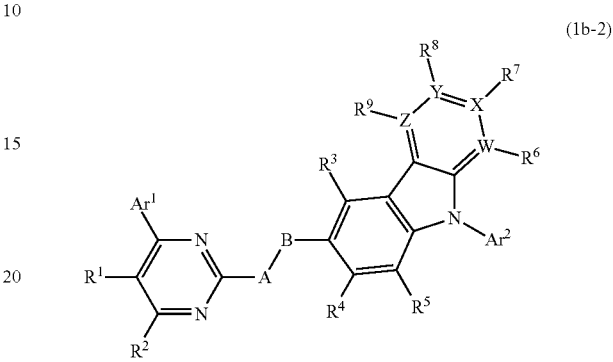

(1b-2)

wherein A, B, Ar$^1$, Ar$^2$, R$^1$ to R$^9$, W, X, Y and Z are as defined above.

The pyrimidine derivatives of the invention represented by the above general formula (1) can be synthesized by, for example, the method described below.

For example, the Suzuki's coupling reaction of a 2,4,6-trichloropyrimidine with an arylboronic acid or an arylboronic acid ester is conducted twice to introduce aryl groups into the fourth and sixth positions of the pyrimidine ring (4,6-diarylpyrimidine).

Further, the Suzuki's coupling reaction of the third time is effected with the arylboronic acid or the arylboronic acid ester to synthesize the pyrimidine derivative of the present invention having the pyrimidine ring structure and the pyridoindole ring structure.

In the above synthesizing method, for example, the Suzuki's coupling reaction of the first or the second time is carried out by using the arylboronic acid or the arylbononic acid ester having the pyridoindole ring structure to thereby synthesize the pyrimidine derivative of the above general formula (1a-1) in which the pyridoindole ring structure is introduced to the fourth position of the pyrimidine ring. The Suzuki's coupling reaction of the third time is carried out by using the arylboronic acid or the arylboronic acid ester having the pyridoindole ring structure to thereby synthesize the pyrimidine derivative of the above general formula (1b-1) in which the pyridoindole ring structure is introduced to the second position of the pyrimidine ring.

The synthesized compounds are refined by column chromatography, by the adsorption refining method using silica gel, activated carbon or activated clay, by the recrystallization method using a solvent or by the crystallization method. Further, the compounds are identified by the NMR analysis.

Described below are concrete examples of the pyrimidine derivatives of the present invention to which only, however, the invention is in no way limited.

(Compound 1)
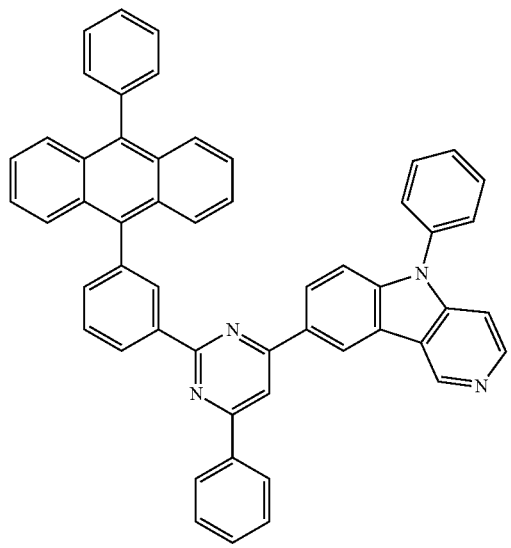
Y = N
A = B = single bond
formula (1a-2)
(Compound 2)
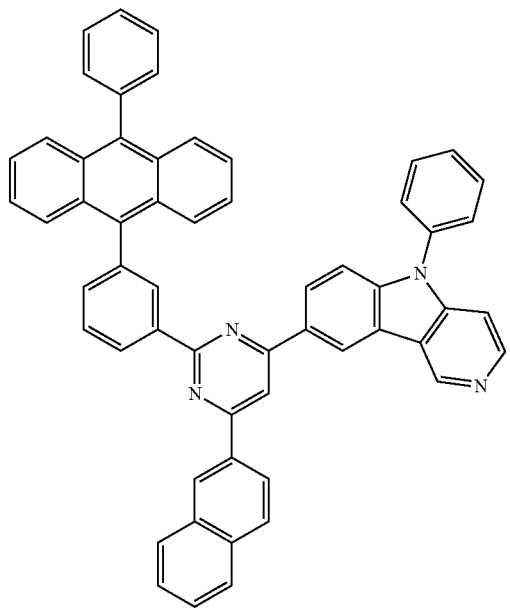
Y = N
A = B = single bond
formula (1a-2)
(Compound 3)
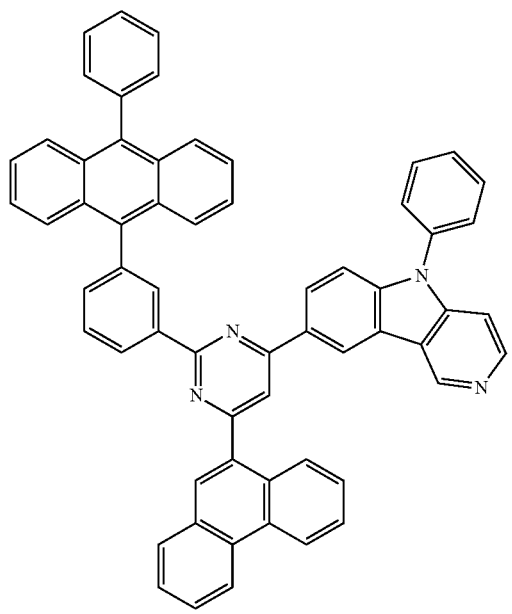
Y = N
A = B = single bond
formula (1a-2)
(Compound 4)
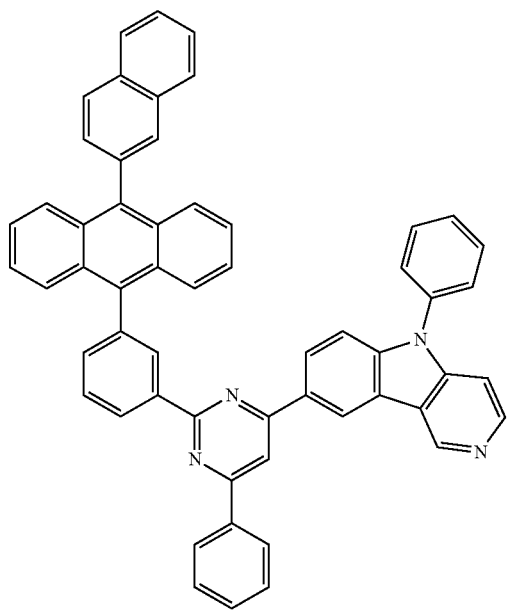
Y = N
A = B = single bond
formula (1a-2)

-continued
(Compound 5)
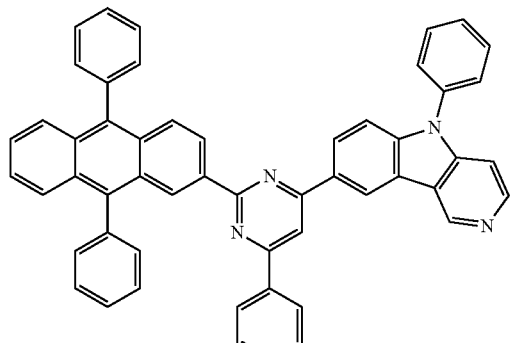
Y = N
A = B = single bond
formula (1a-2)
(Compound 6)
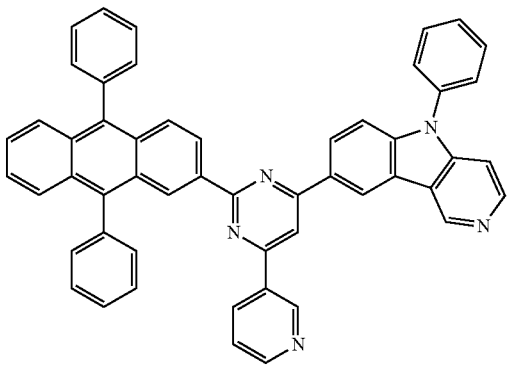
Y = N
A = B = single bond
formula (1a-2)
(Compound 7)
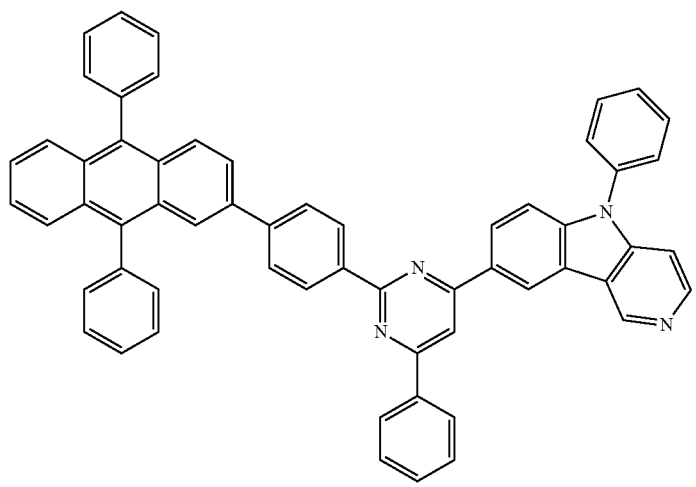
Y = N
A = B = single bond
formula (1a-2)
(Compound 8)
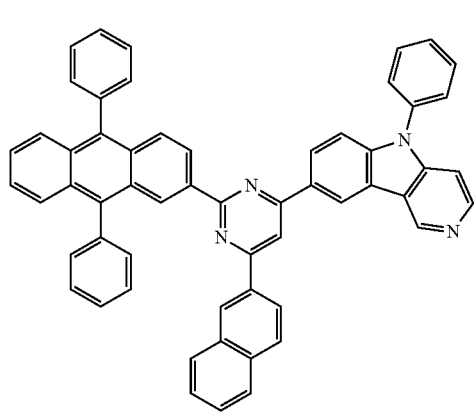
Y = N
A = B = single bond
formula (1a-2)
(Compound 9)
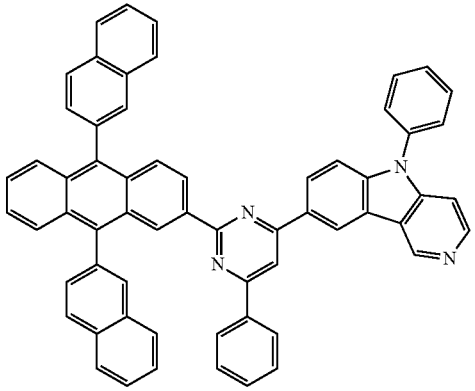
Y = N
A = B = single bond
formula (1a-2)

(Compound 10)
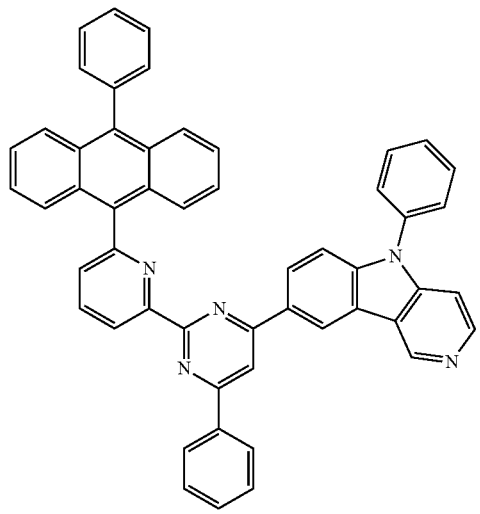
Y = N
A = B = single bond
formula (1a-2)
(Compound 11)
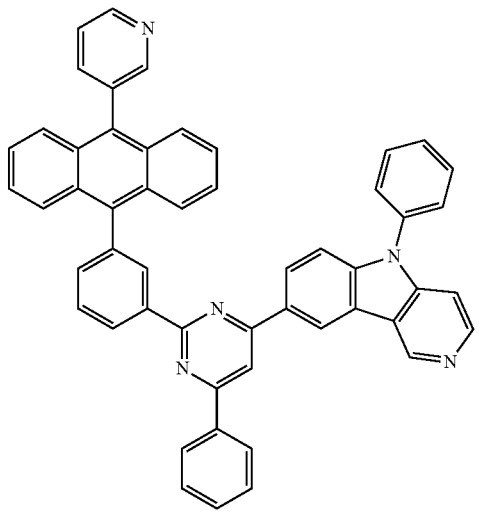
Y = N
A = B = single bond
formula (1a-2)
(Compound 12)
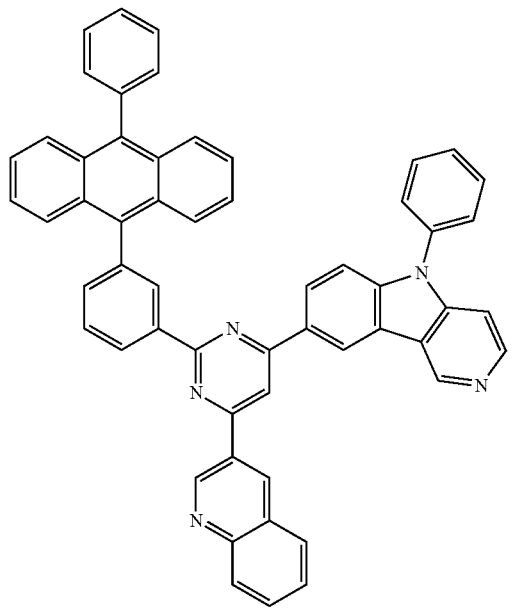
Y = N
A = B = single bond
formula (1a-2)

(Compound 13)
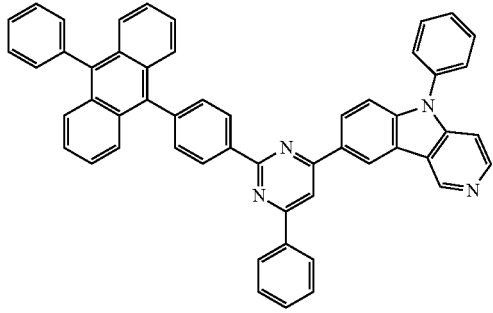
Y = N
A = B = single bond
formula (1a-2)
(Compound 14)
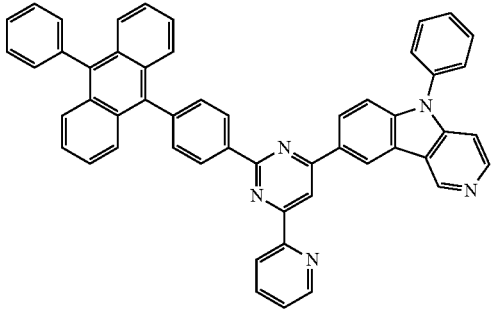
Y = N
A = B = single bond
formula (1a-2)
(Compound 15)
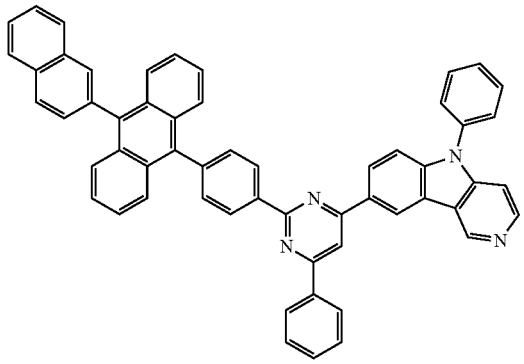
Y = N
A = B = single bond
formula (1a-2)
(Compound 16)
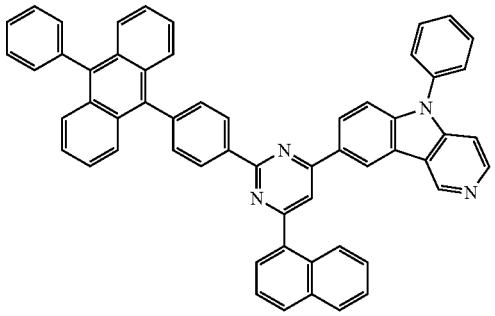
Y = N
A = B = single bond
formula (1a-2)
(Compound 17)
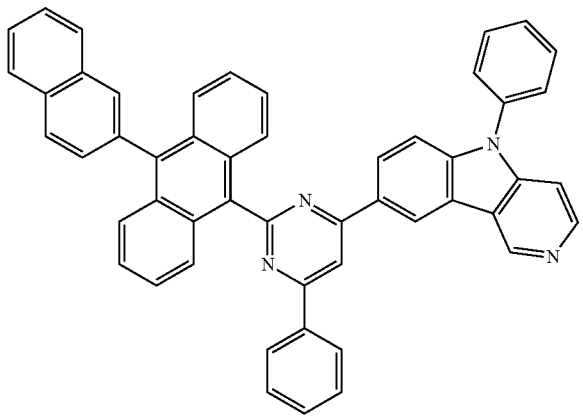
Y = N
A = B = single bond
formula (1a-2)

-continued
(Compound 18)
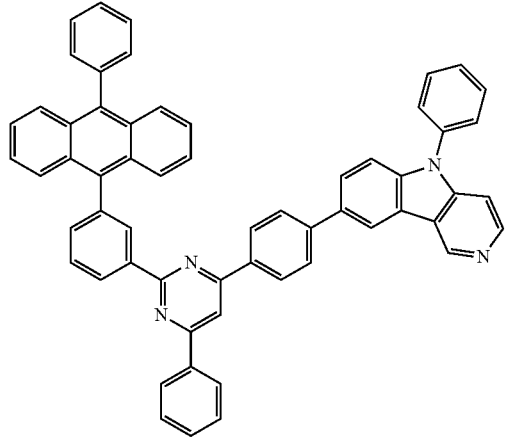
Y = N
A or B = single bond
formula (1a-2)
(Compound 19)
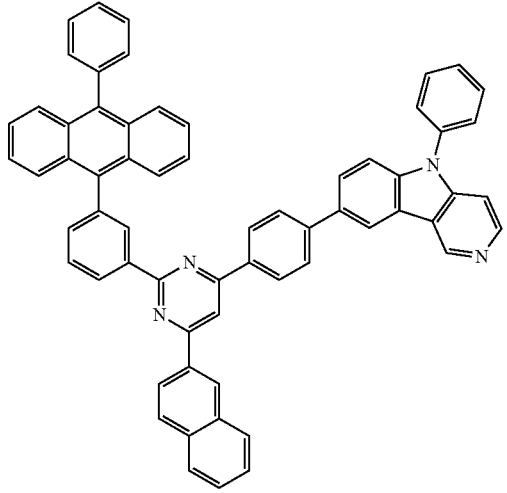
Y = N
A or B = single bond
formula (1a-2)
(Compound 20)
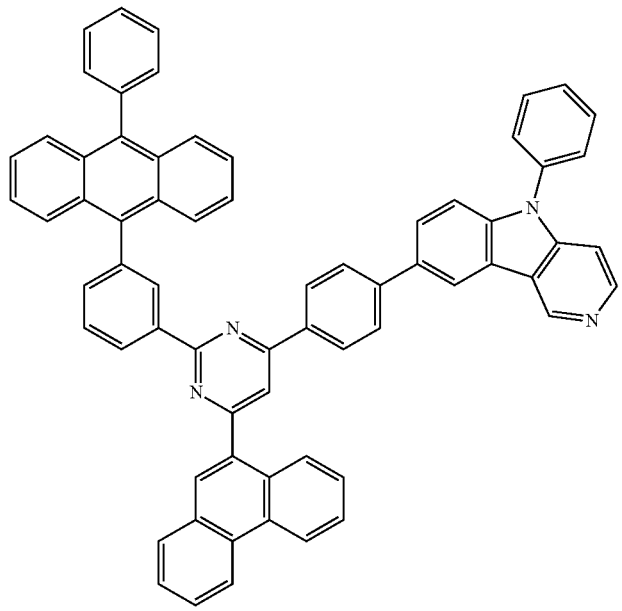
Y = N
A or B = single bond
formula (1a-2)

(Compound 21)
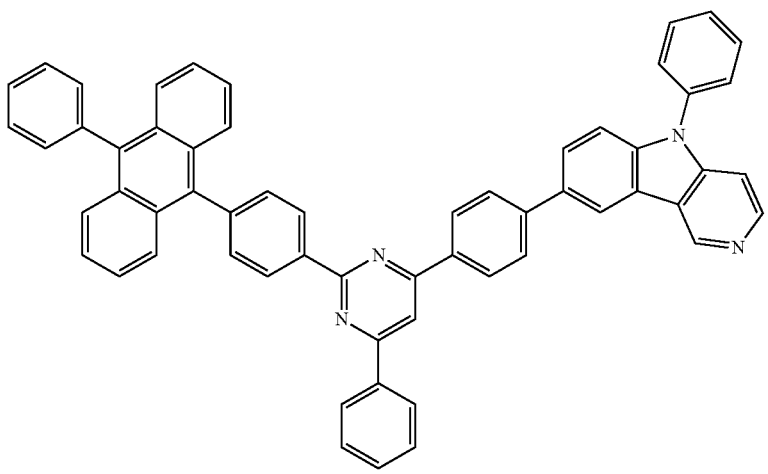
Y = N
A or B = single bond
formula (1a-2)
(Compound 22)
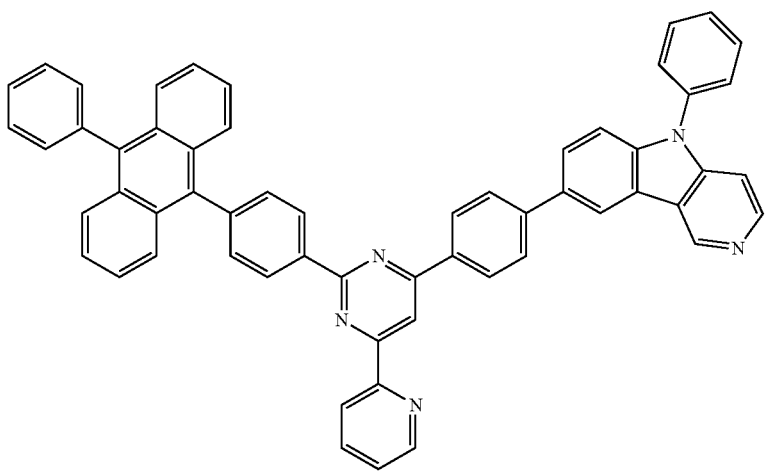
Y = N
A or B = single bond
formula (1a-2)
(Compound 23)
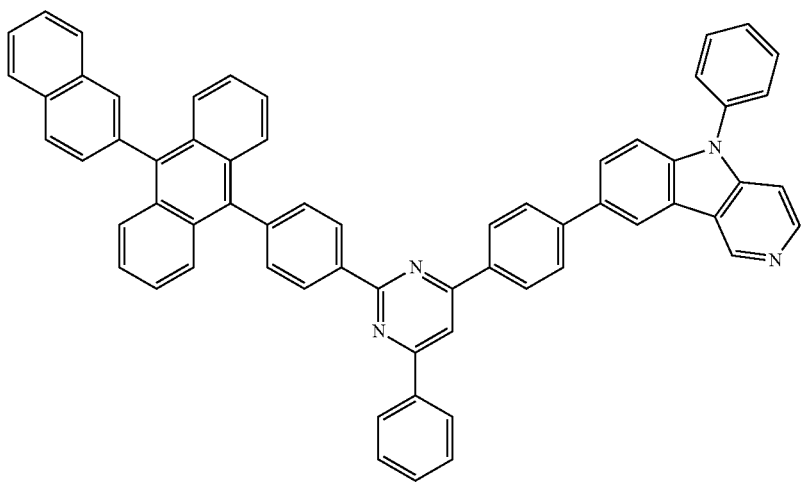
Y = N
A or B = single bond
formula (1a-2)

-continued
(Compound 24)
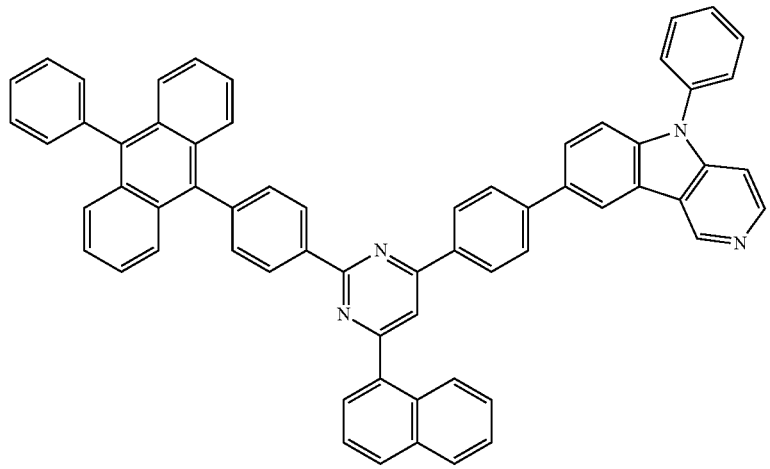
Y = N
A or B = single bond
formula (1a-2)
(Compound 25)
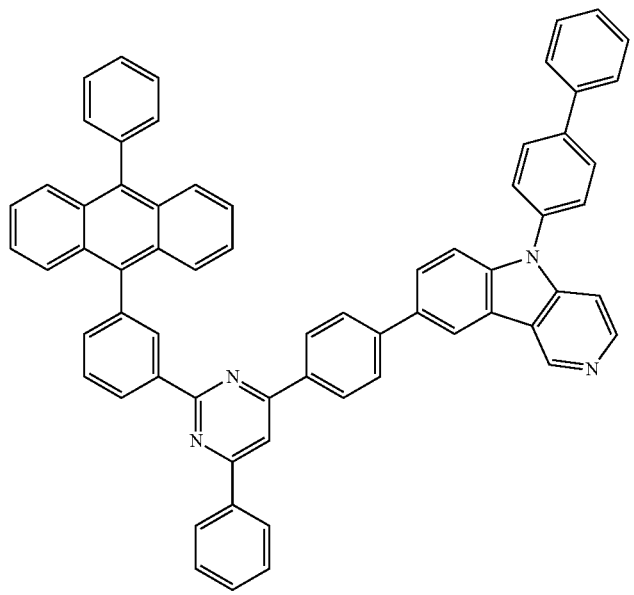
Y = N
A or B = single bond
formula (1a-2)

(Compound 26)
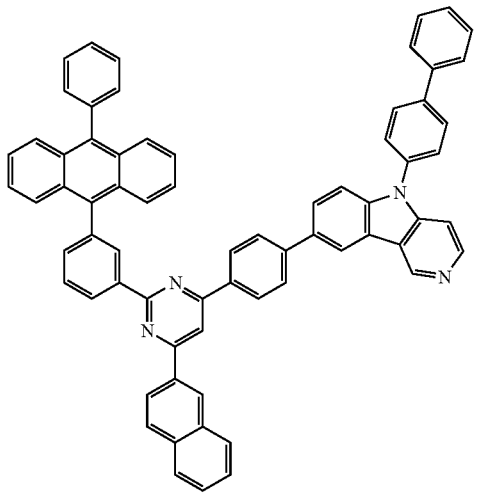
Y = N
A or B = single bond
formula (1a-2)
(Compound 27)
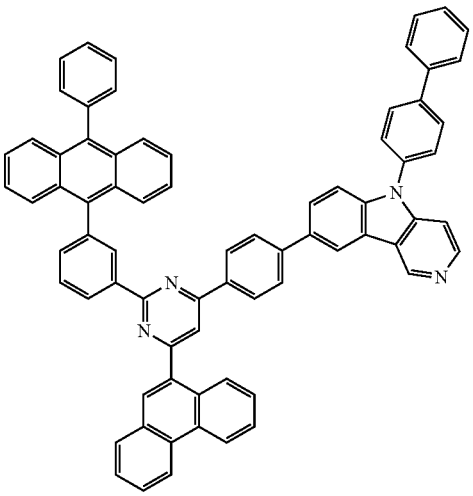
Y = N
A or B = single bond
formula (1a-2)
(Compound 28)
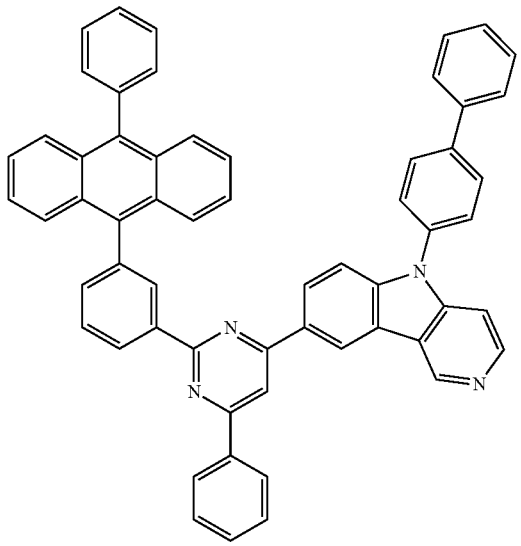
Y = N
A or B = single bond
formula (1a-2)

(Compound 29)
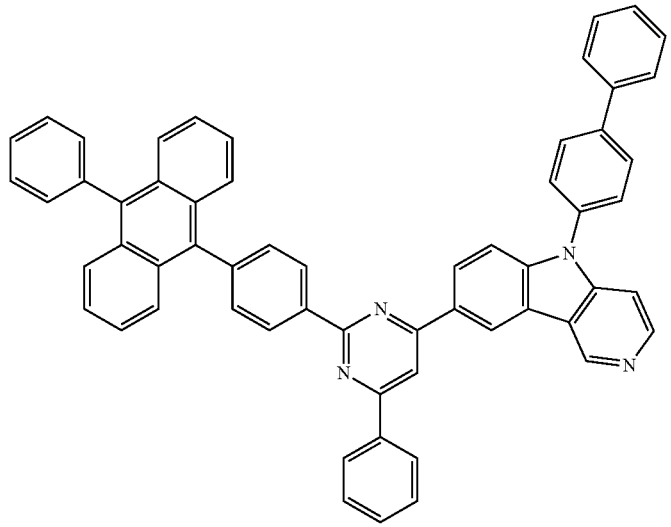
Y = N
A = B = single bond
formula (1a-2)
(Compound 30)
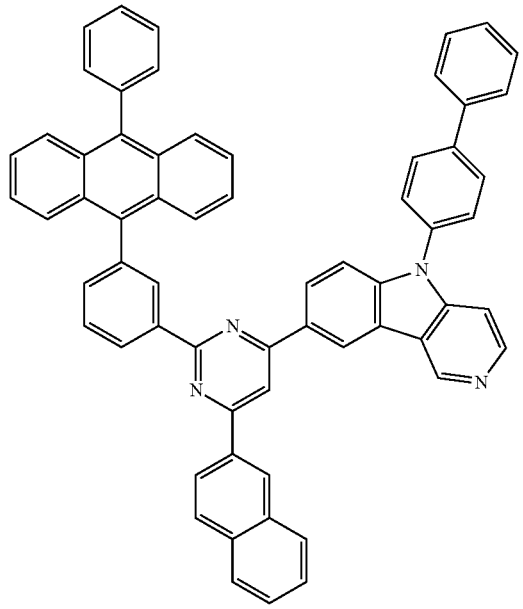
Y = N
A = B = single bond
formula (1a-2)

(Compound 31)
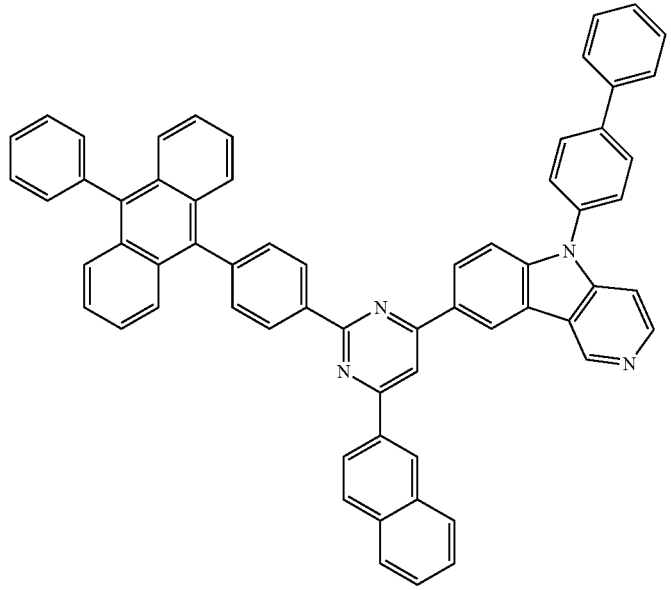
Y = N
A = B = single bond
formula (1a-2)
(Compound 32)
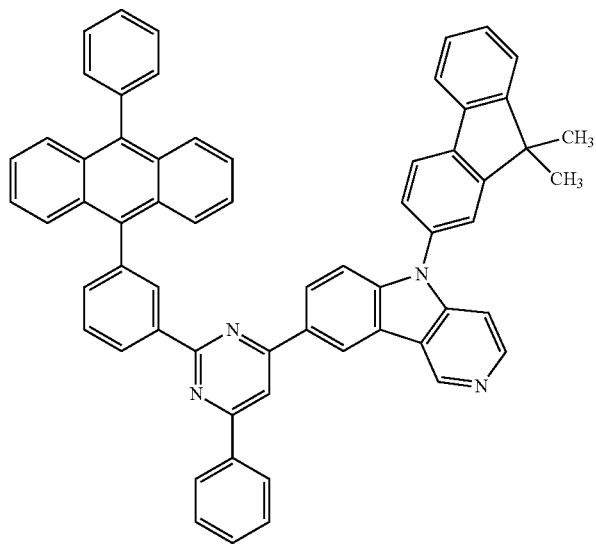
Y = N
A = B = single bond
formula (1a-2)

-continued
(Compound 33)
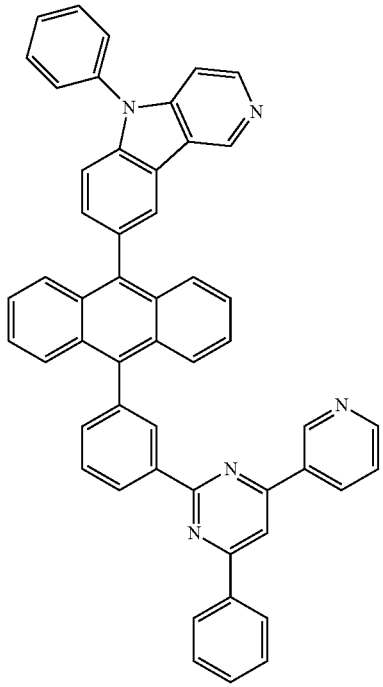
Y = N
formula (1b-2)
(Compound 34)
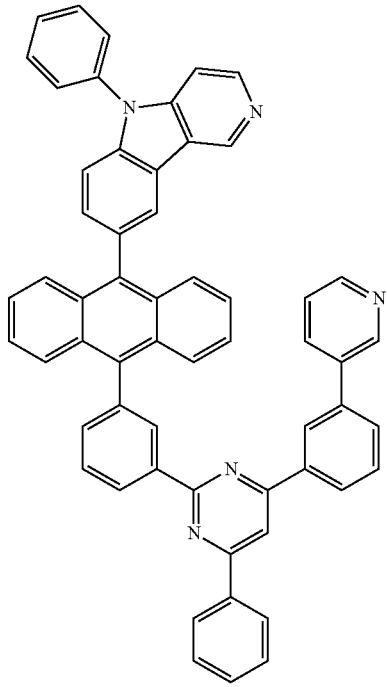
Y = N
formula (1b-2)
(Compound 35)
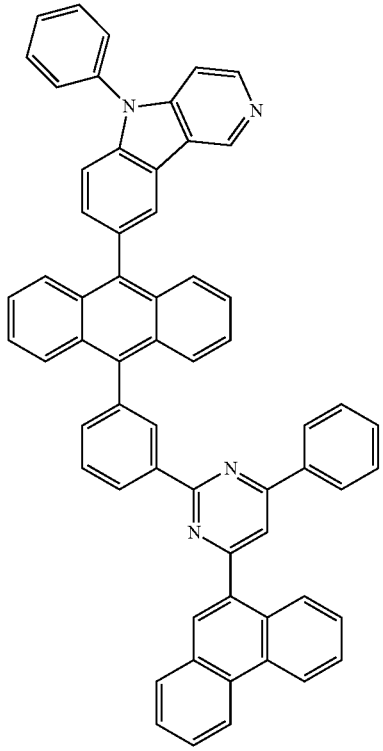
Y = N
formula (1b-2)
(Compound 36)
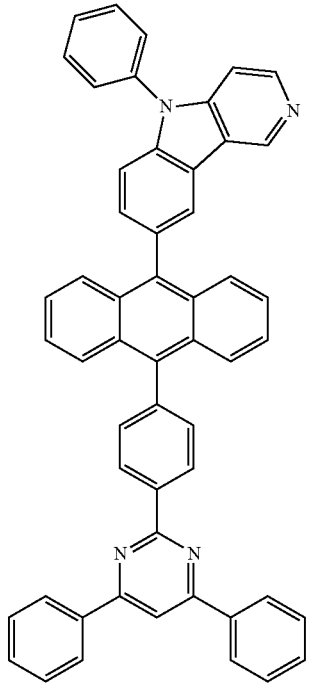
Y = N
formula (1b-2)

-continued
(Compound 37)
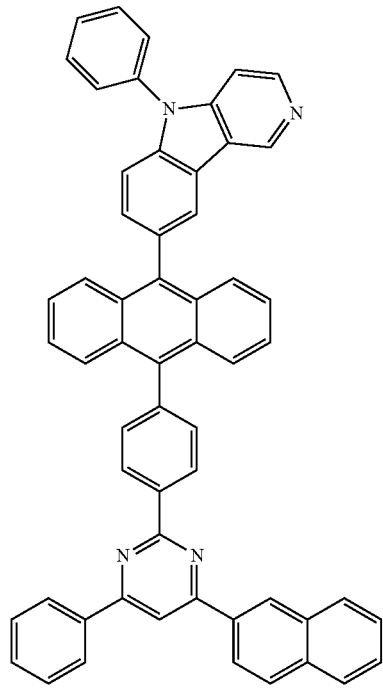
Y = N
formula (1b-2)
(Compound 38)
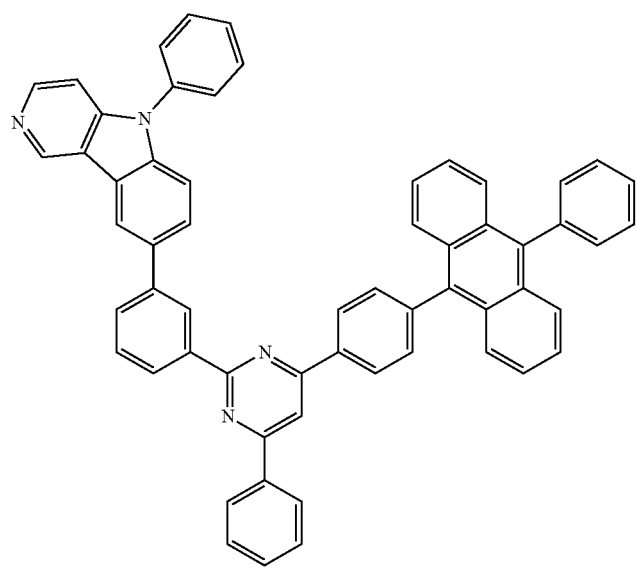
Y = N
A or B = single bond
formula (1b-2)

(Compound 39)
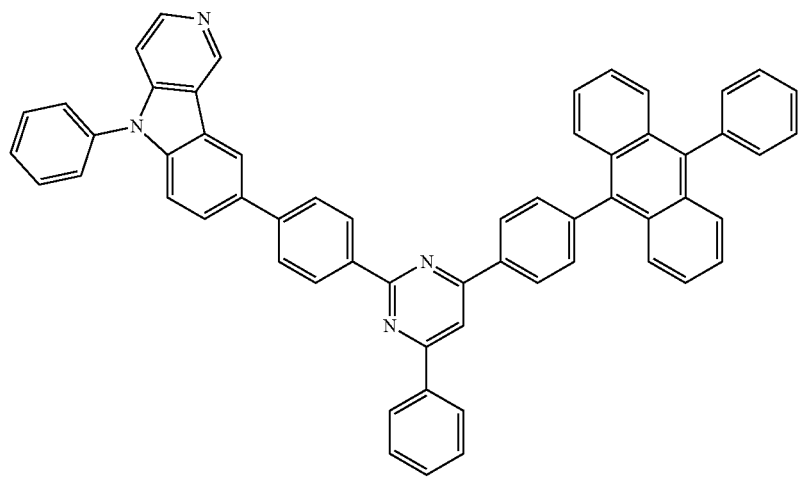
Y = N
A or B = single bond
formula (1b-2)
(Compound 40)
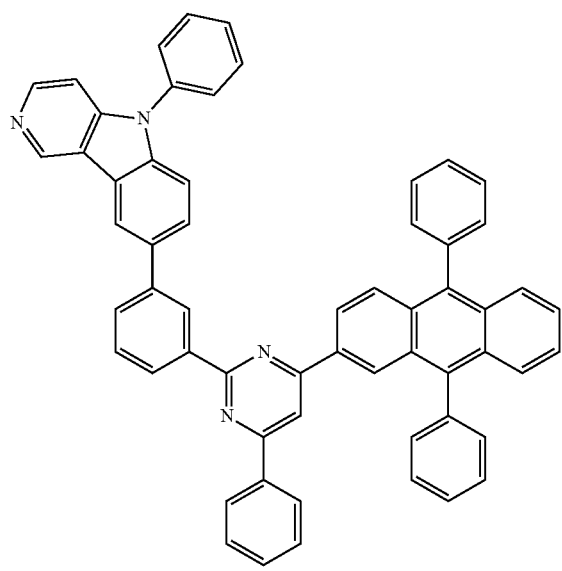
Y = N
A or B = single bond
formula (1b-2)
(Compound 41)
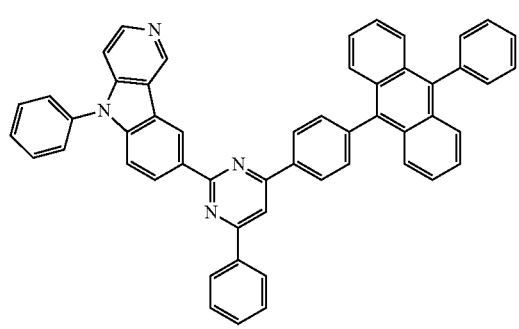
Y = N
A = B = single bond
formula (1b-2)
(Compound 42)
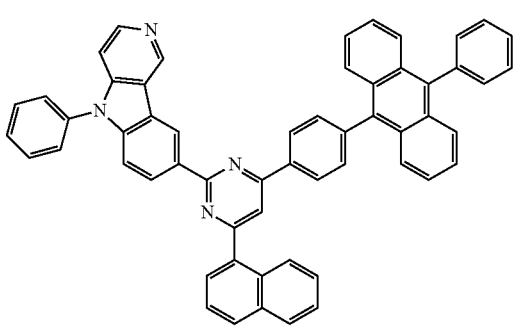
Y = N
A = B = single bond
formula (1b-2)

(Compound 43)
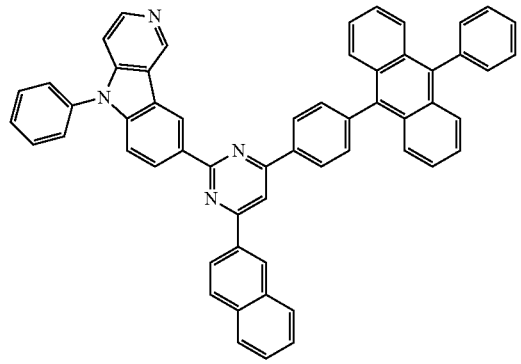
Y = N
A = B = single bond
formula (1b-2)
(Compound 44)
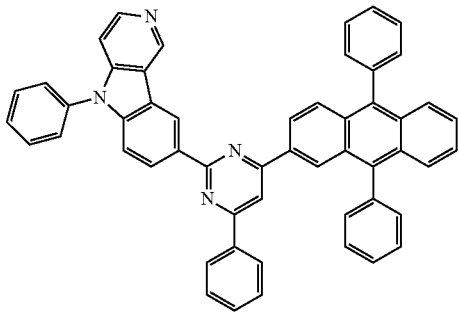
Y = N
A = B = single bond
formula (1b-2)
(Compound 45)
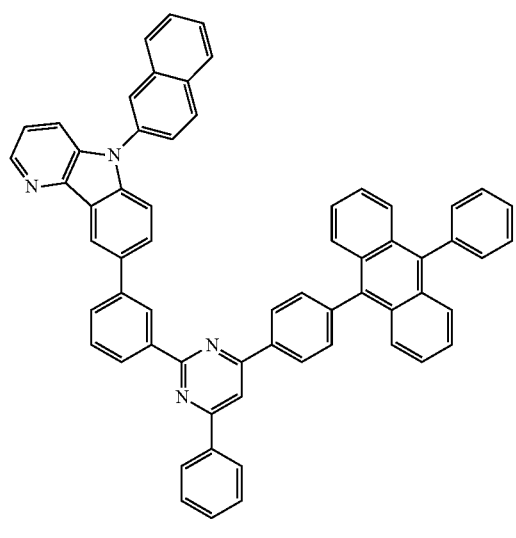
Z = N
A or B = single bond
formula (1b-2)
(Compound 46)
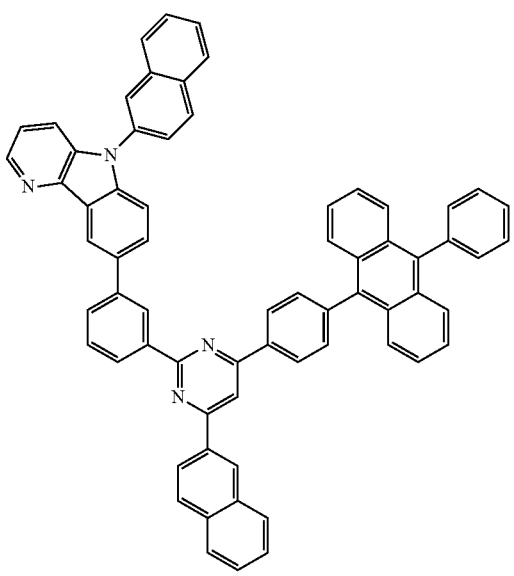
Z = N
A or B = single bond
formula (1b-2)

(Compound 47)
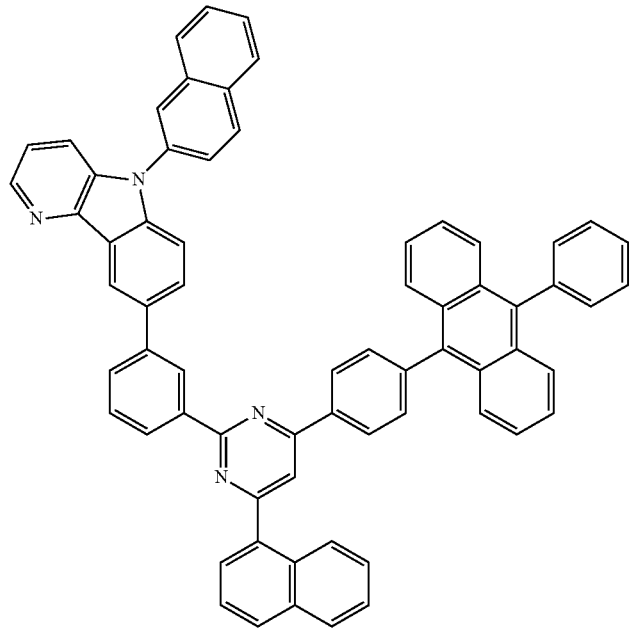
Z = N
A or B = single bond
formula (1b-2)
(Compound 48)
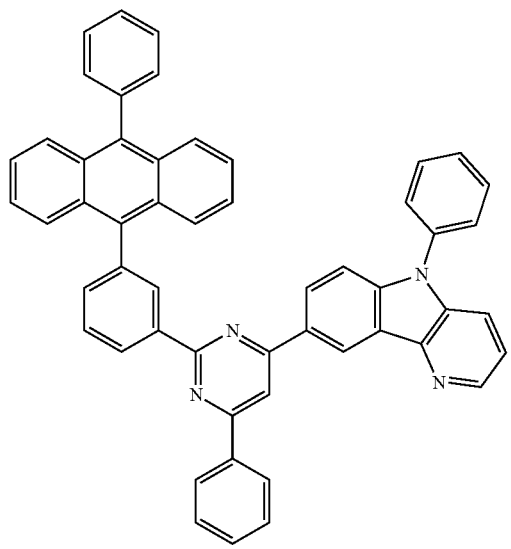
Z = N
A = B = single bond
formula (1a-2)
(Compound 49)
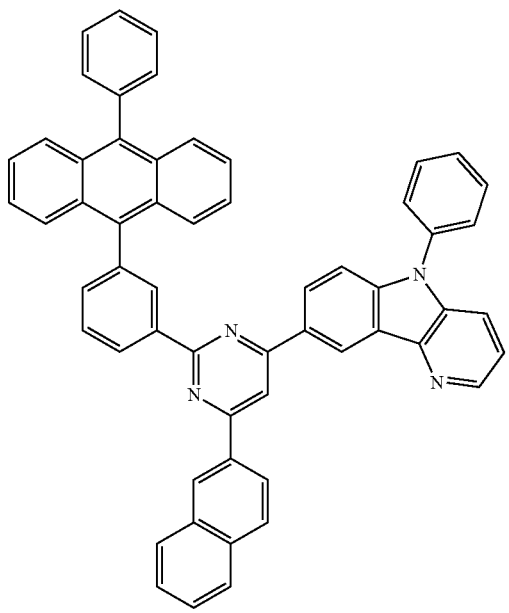
Z = N
A = B = single bond
formula (1a-2)

(Compound 50)
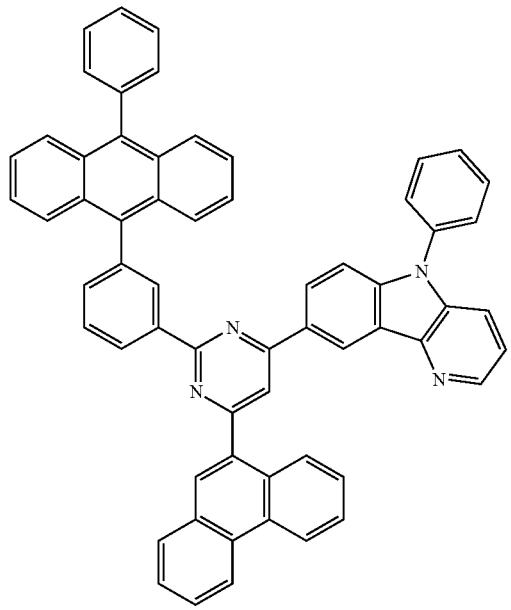
Z = N
A = B = single bond
formula (1a-2)
(Compound 51)
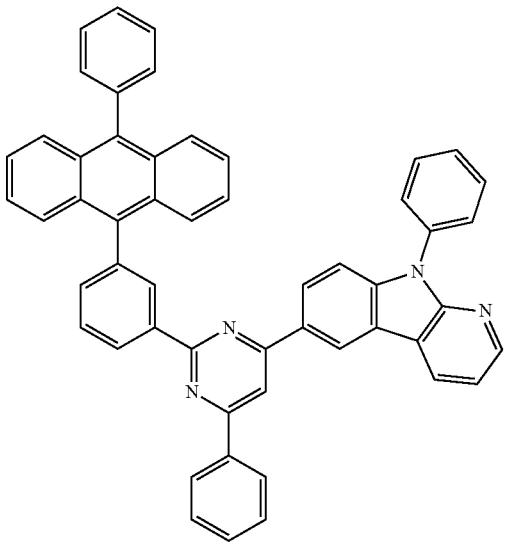
W = N
A = B = single bond
formula (1a-2)
(Compound 52)
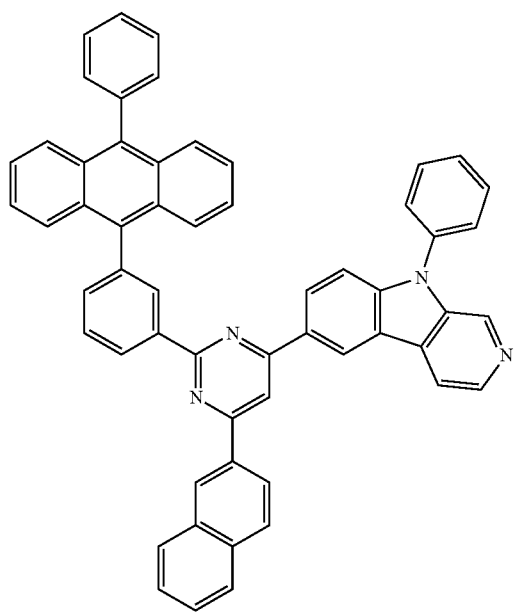
X = N
A = B = single bond
formula (1a-2)

(Compound 53)
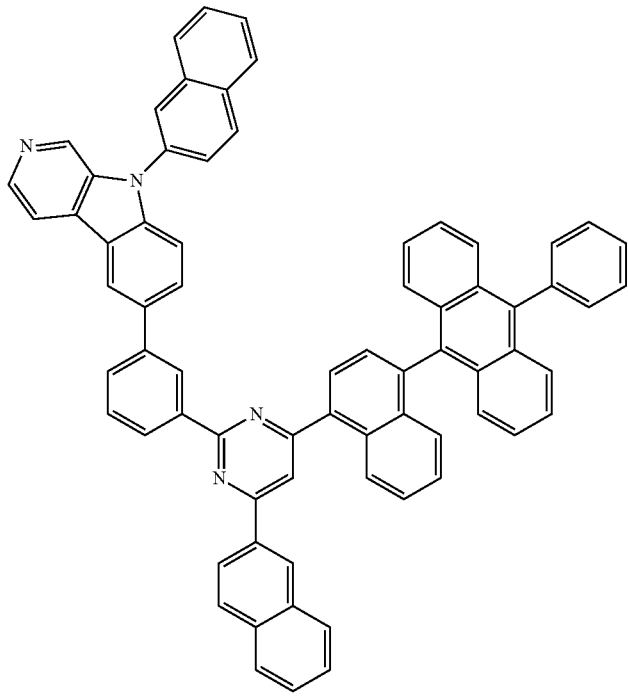
X = N
A or B = single bond
formula (1b-2)
(Compound 54)
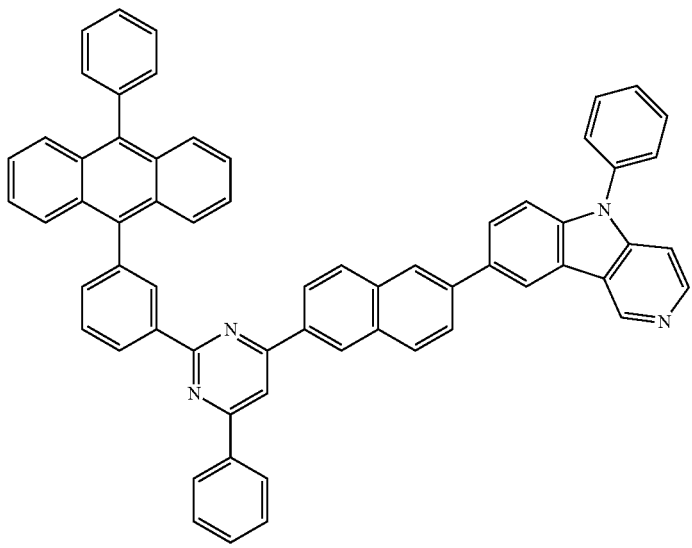
Y = N
A or B = single bond
formula (1a-2)

(Compound 55)
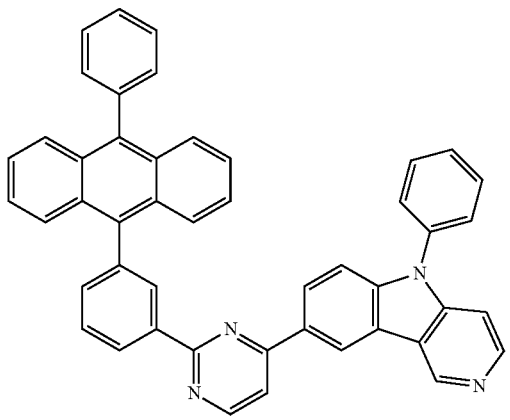
Y = N
A = B = single bond
formula (1a-2)
(Compound 56)
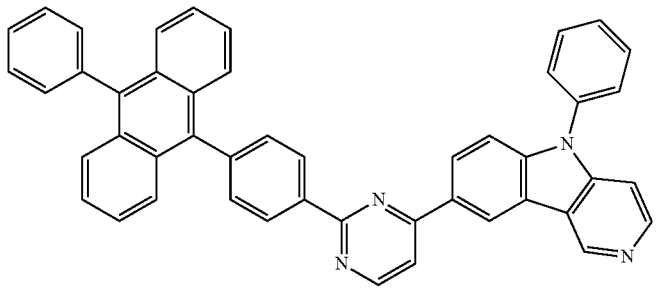
Y = N
A = B = single bond
formula (1a-2)
(Compound 57)
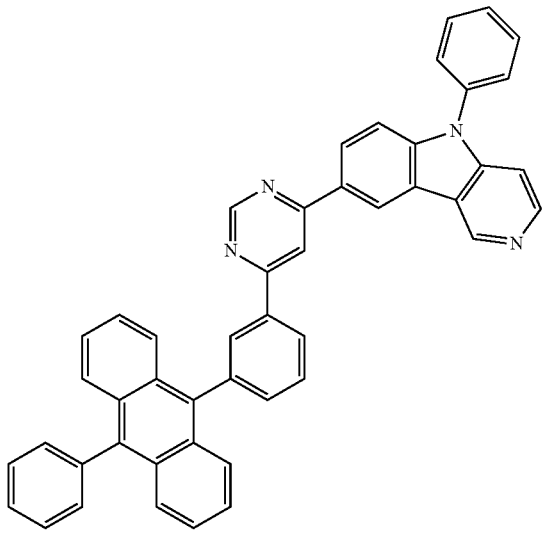
Y = N
A = B = single bond
formula (1a-1)

(Compound 59)
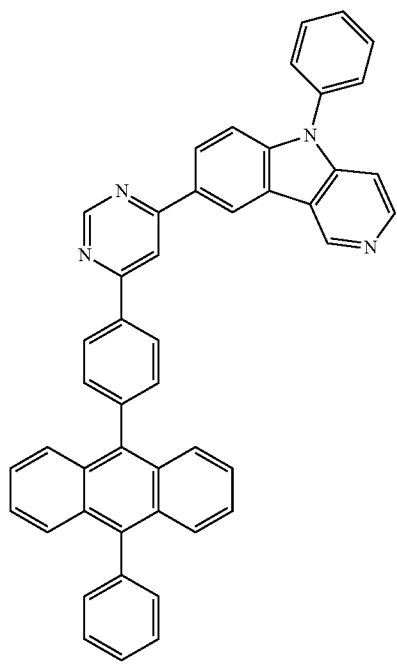
Y = N
A = B = single bond
formula (1a-1)
(Compound 58)
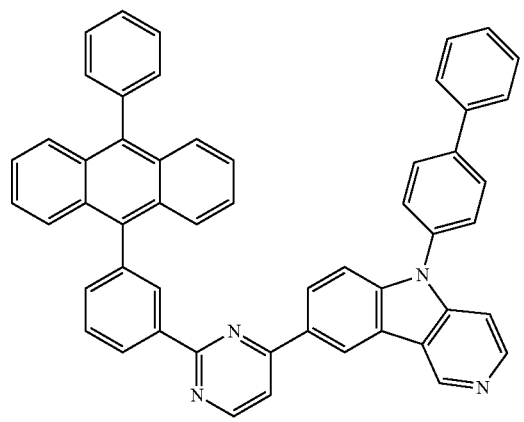
Y = N
A = B = single bond
formula (1a-2)
(Compound 60)
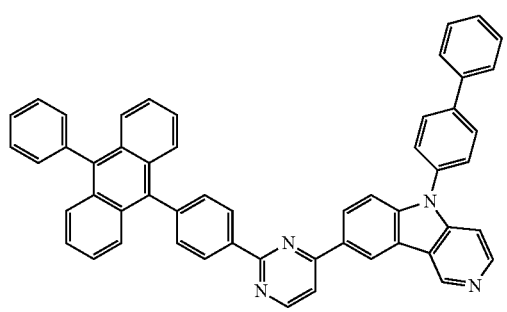
Y = N
A = B = single bond
formula (1a-2)
(Compound 61)
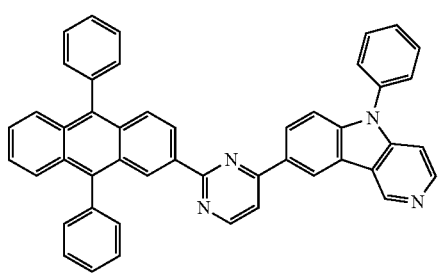
Y = N
A = B = single bond
formula (1a-2)

(Compound 62)
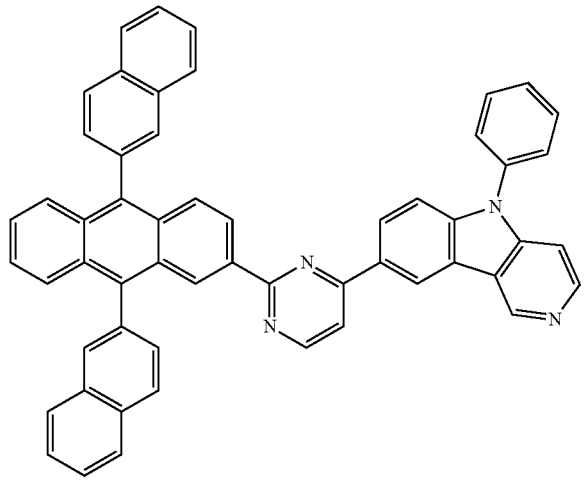
Y = N
A = B = single bond
formula (1a-2)
(Compound 63)
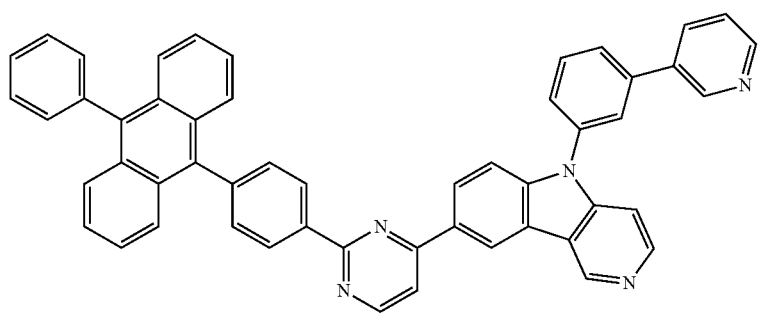
Y = N
A = B = single bond
formula (1a-2)
(Compound 64)
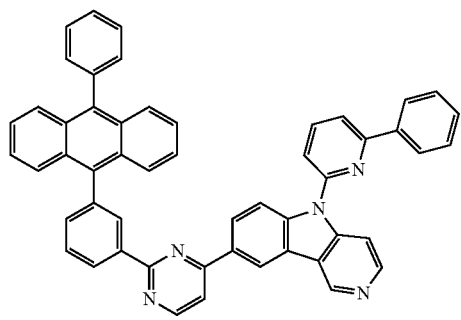
Y = N
A = B = single bond
formula (1a-2)
(Compound 65)
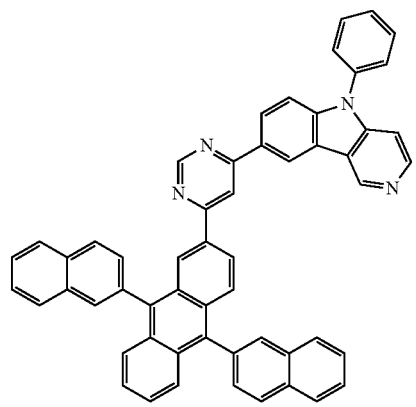
Y = N
A = B = single bond
formula (1a-1)

(Compound 66)
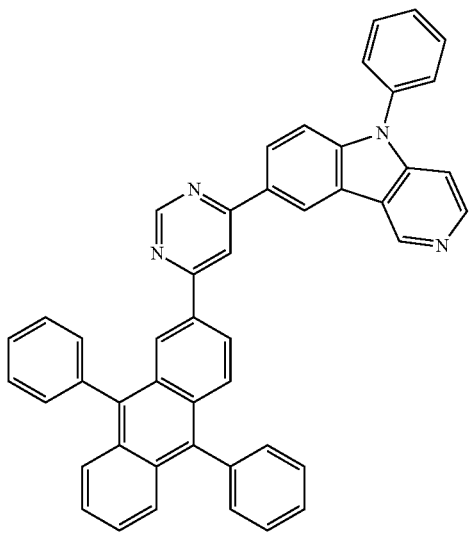
Y = N
A = B = single bond
formula (1a-1)
(Compound 67)
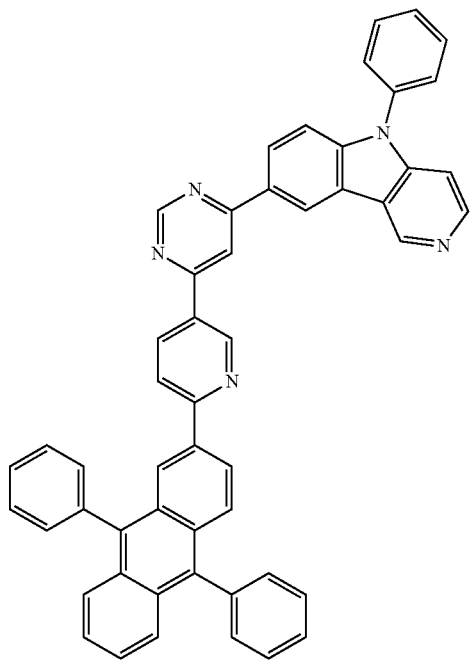
Y = N
A = B = single bond
formula (1a-1)
(Compound 68)
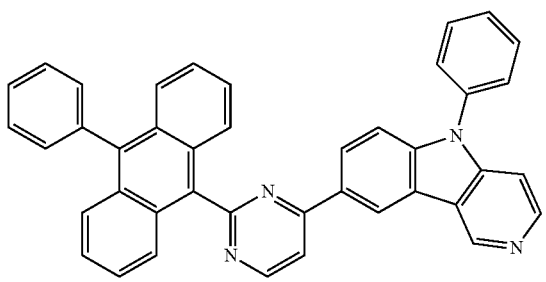
Y = N
A = B = single bond
formula (1a-2)

-continued
(Compound 69)
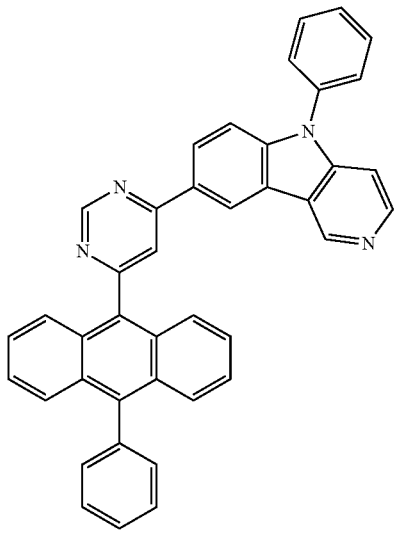
Y = N
A = B = single bond
formula (1a-1)
(Compound 70)
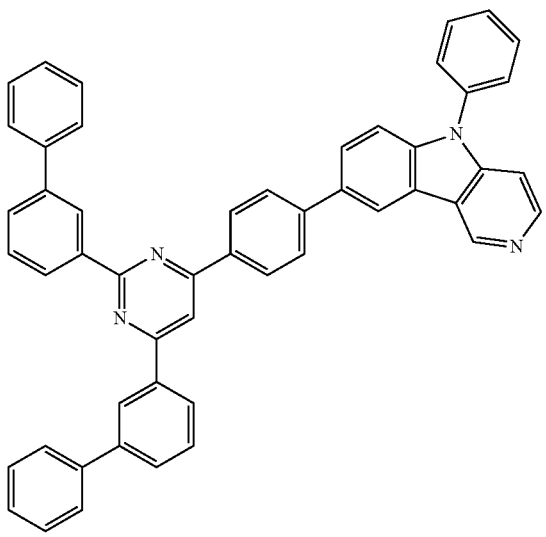
Y = N
A = B = single bond
formula (1a-2)

(Compound 71)
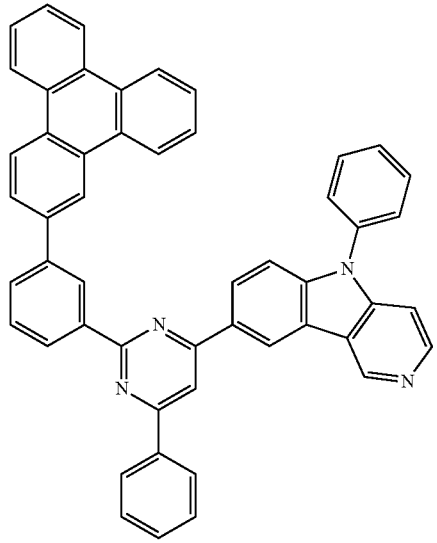
Y = N
A = B = single bond
formula (1a-2)
(Compound 72)
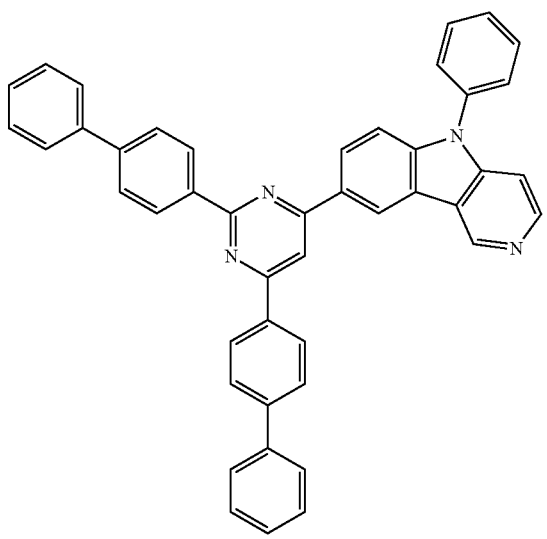
Y = N
A = B = single bond
formula (1a-2)
(Compound 73)
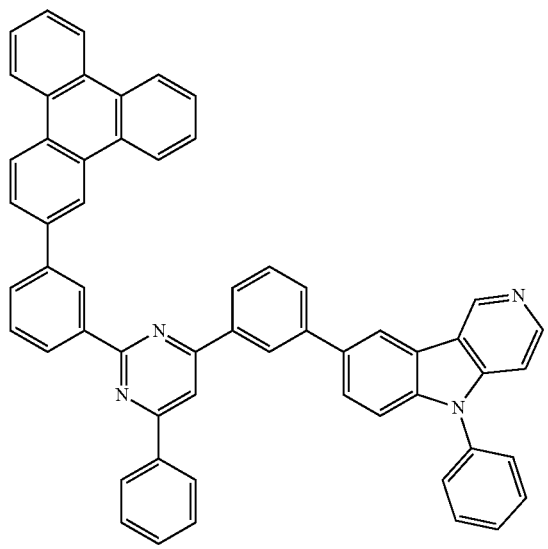
Y = N
A = B = single bond
formula (1a-2)

(Compound 74)

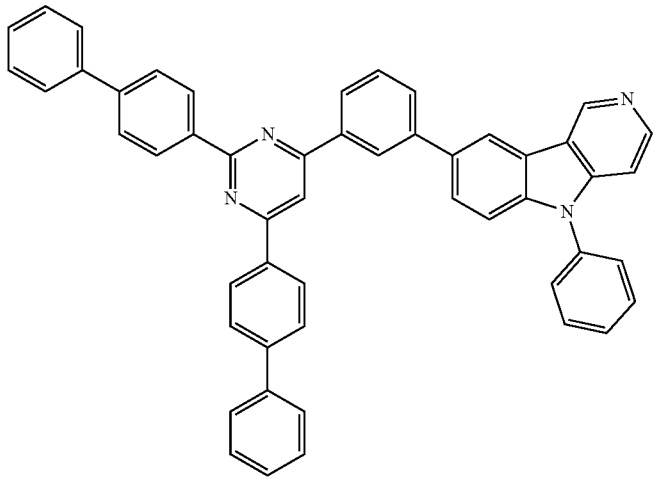

Y = N
A or B = single bond
formula (1a-2)

(Compound 75)

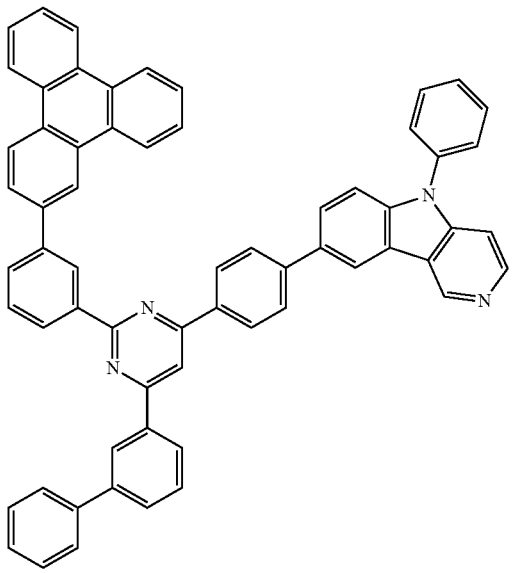

Y = N
A or B = single bond
formula (1a-2)

(Compound 76)

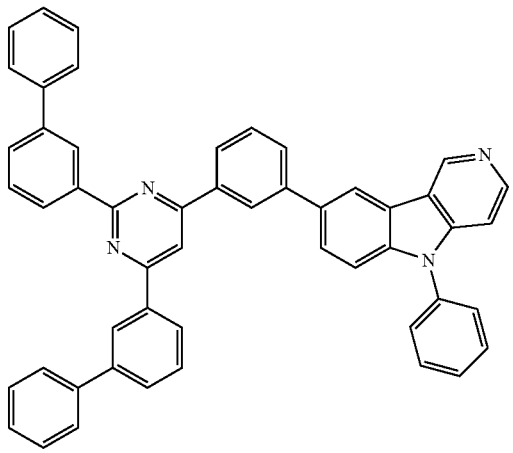

Y = N
A or B = single bond
formula (1a-2)

The above pyrimidine derivatives of the present invention have high glass transition points (Tg) (e.g., not lower than 100° C. and, specifically, not lower than 130° C.), make it possible to form a thin film having excellent heat resistance, stably maintain amorphous state and, therefore, stably maintain the state of a thin film. Besides, the pyrimidine derivatives of the invention feature large electron injection rates, high electron migrating rates and high hole-blocking power. Therefore, if the compound of the present invention is deposited to form a film of a thickness of 100 nm and if the film is measured for its work function, a very high value is exhibited.

<Organic EL Devices>

Figure 4:
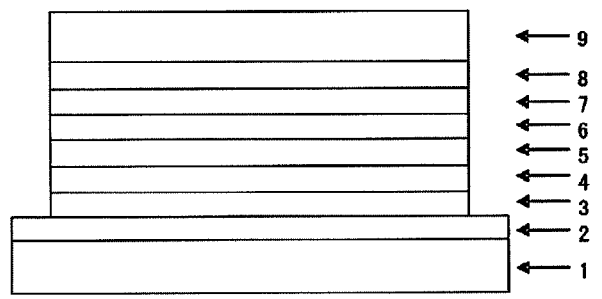
FIG. 4 is a view illustrating the structure of EL devices of Examples 6 to 9 and Comparative Examples 1 and 2.

The organic EL device having the organic layer formed by using the above pyrimidine derivative of the present invention has a structure as shown, for example, in FIG. 4.

Namely, a transparent anode 2, a hole injection layer 3, a hole-transporting layer 4, a luminous layer 5, a hole-blocking layer 6, an electron-transporting layer 7, an electron injection layer 8 and a cathode 9 are formed on a glass substrate 1 (which may be any transparent substrate such as transparent resin substrate or the like substrate).

The organic EL device to which the pyrimidine derivative of the present invention is applied is not limited to the one of the above layer structure, as a matter of course. For instance, the organic EL device may have an electron-blocking layer formed between the hole-transporting layer 4 and the luminous layer 5, or may have a simplified layer structure omitting the electron injection layer 8 or the hole injection layer 3. For instance, some layers can be omitted from the above multilayer structure. Namely, the organic EL device can be fabricated in a simple layer structure having the anode 2, hole-transporting layer 4, luminous layer 5, electron-transporting layer 7 and cathode 9 formed on the substrate 1.

That is, the pyrimidine derivative of the invention is preferably used as a material for forming organic layers (e.g., luminous layer 5, hole-blocking layer 6, electron-transporting layer 7 and electron injection layer 8) between the anode 2 and the cathode 9.

In the organic EL device, the transparent anode 2 may be formed by using an electrode material which has been known per se, i.e., by vapor-depositing an electrode material having a large work function, such as ITO or gold on the substrate 1 (transparent substrate such as glass substrate or the like).

Further, the hole injection layer 3 can be formed on the transparent anode 2 by using the materials that have been known per se, such as those described below.

Porphyrin compound as represented by copper phthalocyanine;

Triphenylamine derivative of the star burst type;

Arylamine having a structure coupled via a single bond or a divalent group without hetero atom (e.g., trimer or tetramer of triphenylamine);

Acceptor-type heterocyclic compounds such as hexacyanoazatriphenylene; and

High molecular materials of the application type, such as poly(3,4-ethylenedioxythiophene) (PEDOT), poly(styrene sulfonate) (PSS), etc.

The layer (thin film) can be formed by using the above materials relying not only upon the vacuum evaporation method but also upon the known methods such as spin-coating method or ink-jet method. The layers described below, too, can similarly be formed by the vacuum evaporation, the spin-coating or the ink-jet method.

The hole-transporting layer 4, too, can be formed on the hole injection layer 3 by using a hole-transporting material that has been known per se. Representative examples of the hole-transporting materials are:

Benzidine derivatives such as,

N,N'-Diphenyl-N,N'-di(m-tolyl)benzidine (hereinafter abbreviated as TPD);

N,N'-Diphenyl-N,N'-di(α-naphthyl)benzidine (hereinafter abbreviated as NPD); and N,N,N',N'-Tetrabiphenylylbenzidine; and Amine derivatives such as, 1,1-Bis[4-(di-4-tolylamino)phenyl]cyclohexane (hereinafter abbreviated as TAPC);

Various triphenylamine trimers and tetramers; and

The above-mentioned application-type high molecular materials that can also be used for forming the hole injection layer.

The compounds for forming the hole-transporting layer may be used alone to form a film or may be used being mixed together in two or more kinds to form a film. Or the above compounds may be used in one kind or in a plurality of kinds to form a plurality of layers, and a multiplicity of films formed by laminating such layers can be used as a hole-transporting layer.

It is, further, allowable to form a layer that serves as both the hole injection layer 3 and the hole-transporting layer 4. The hole injection•transporting layer can be formed by being coated with a high molecular material such as poly(3,4-ethylenedioxythiophene) (hereinafter abbreviated as PEDOT) or polystyrene sulfonate (hereinafter abbreviated as PSS).

In forming the hole-transporting layer 4 (the same holds for the hole injection layer 3, too), the material usually used for forming the layer may, further, be P-doped with a trisbromophenylaminehexachloroantimony or the like. It is also allowable to form the hole-transporting layer 4 (or the hole injection layer 3) by using a high molecular compound having a basic skeleton of TPD.

Further, as the electron-blocking layer (that can be formed between the hole-transporting layer 4 and the luminous layer 5) that has not been shown, there can be used a known electron-blocking compound having the electron-blocking action, such as carbazole derivative or a compound that has a triphenylsilyl group and has a triarylamine structure. Described below are concrete examples of the carbazole derivative and the compound having the triarylamine structure.

<Carbazole Derivatives>

4,4',4"-Tri(N-carbazolyl)triphenylamine (hereinafter abbreviated as TCTA);

9,9-Bis[4-(carbazole-9-il)phenyl]fluorene;

1,3-Bis(carbazole-9-il)benzene (hereinafter abbreviated as mCP); and 2,2-Bis(4-carbazole-9-ilphenyl)adamantane (hereinafter abbreviated as Ad-Cz).

<Compounds Having a Triarylamine Structure>

9-[4-(Carbazole-9-il)phenyl]-9-[4-(triphenylsilyl)phenyl]-9H-fluorene.

The electron-blocking layer is formed by using one, two or more kinds of the above known electron-blocking materials. It is, however, also allowable to form a plurality of layers by using one or a plurality of kinds of the electron-blocking materials, and use a multiplicity of films formed by laminating such layers as the electron-blocking layer.

The luminous layer 5 of the organic EL device can be formed by using the pyrimidine derivative of the invention as the luminous material. The luminous layer 5, however, can also be formed by using a metal complex of a quinolynol derivative as represented by $Alq_3$ as well as various metal complexes such as of zinc, beryllium and aluminum, and luminous materials such as anthracene derivative, bisstyrylbenzene derivative, pyrene derivative, oxazole derivative and polyparaphenylenevinylene derivative.

It is also allowable to constitute the luminous layer 5 by using a host material and a dopant material.

As the host material in this case, there can be used thiazole derivative, benzimidazole derivative and polydialkylfluorene derivative in addition to the above luminous materials.

As the dopant material, there can be used quinacridone, cumalin, rubrene, perylene and derivatives thereof, benzopyran derivative, Rhodamine derivative and aminostyryl derivative.

The luminous layer 5 too, can be formed in a single-layer structure or in a multi-layer structure in which a plurality of layers are laminated by using one or two or more kinds of the luminous materials.

It is, further, allowable to form the luminous layer 5 by using a phosphorescent luminous material as the luminous material.

As the phosphorescent luminous material, there can be used a phosphorescent luminous body of a metal complex such as of iridium or platinum. For example, there can be used a green luminous phosphor such as $Ir(ppy)_3$, a blue luminous phosphor such as Flrpic or $Flr_6$, and a red luminous phosphor such as $Btp_2Ir(acac)$. These phosphorescent luminous materials are used by being added to the hole injection•transporting host material or to the electron-transporting host material.

As the hole injection•transporting host material, there can be used carbazole derivatives such as 4,4'-di(N-carbazolyl)

biphenyl (hereinafter abbreviated as CBP), TCTA or mCP as well as the pyrimidine derivatives of the invention.

As the electron-transporting host material, there can be used p-bis(triphenylsilyl)benzene (hereinafter abbreviated as UGH2) or 2,2',2''-(1,3,5-phenylene)-tris(1-phenyl-1H-benzimidazole) (hereinafter abbreviated as TPBI).

To avoid the concentration quenching, the host material is desirably doped with the phosphorescent luminous material in an amount in a range of 1 to 30% by weight relative to the whole luminous layer relying on the vacuum coevaporation.

As the luminous material, further, it is also allowable to use a material that emits retarded fluorescence, such as CDCB derivative like PIC-TRZ, CC2TA, PXZ-TRZ or 4CzIPN (see Appl. Phys. Let., 98, 083302 (2011)).

The hole-blocking layer 6 can also be formed between the luminous layer 5 and the electron-transporting layer 7 by using a known compound having the hole-blocking action in addition to using the pyrimidine derivative of the present invention.

As the known compounds having the hole-blocking action, there can be exemplified the following compounds.

Phenanthroline derivatives such as bathocuproin (hereinafter abbreviated as BCP) and the like;

Metal complexes of quinolinol derivatives such as aluminum (III) bis(2-methyl-8-quinolinato)-4-phenylphenolate (hereinafter abbreviated as BAlq) and the like;

Various rare earth complexes;

Triazole derivatives;

Triazine derivatives; and

Oxadiazole derivatives.

These materials can also be used for forming the electron-transporting layer 7 that will be described below. Moreover, the hole-blocking layer 6 and the electron-transporting layer 7 can be formed as one layer.

The hole-blocking layer 6, too, can be formed in the structure of a single layer or of a laminate of a multiplicity of layers, the layers being formed by using one kind of or two or more kinds of the above-mentioned compounds having hole-blocking action.

The electron-transporting layer 7 can be formed by using electron-transporting compounds that have been known per se. such as metal complexes of quinolinol derivatives like Alq$_3$, BAlq, as well as various metal complexes, triazole derivatives, triazine derivatives, oxadiazole derivatives, thiadiazole derivatives, carbodiimide derivatives, quinoxaline derivatives, phenanthroline derivatives and silole derivatives in addition to using the pyrimidine derivatives of the present invention.

The electron-transporting layer 7, too, can be formed in the structure of a single layer or of a laminate of a multiplicity of layers, the layers being formed by using one kind of or two or more kinds of the above-mentioned electron-transporting compounds.

The electron injection layer 8, too, can be formed by using known compounds, i.e., by using alkali metal salts such as lithium fluoride and cesium fluoride, alkaline earth metal salts such as magnesium fluoride, and metal oxides such as aluminum oxide in addition to using the pyrimidne derivatives of the present invention.

As the electron injection layer 8 or the electron-transporting layer 7, further, it is also allowable to use the material that has usually been used for forming these layers but which is, further, N-doped with a metal such as cesium or the like.

As the cathode 9 of the organic EL device, there can be used an electrode material having a low work function, such as aluminum, or an electrode material of an alloy having a lower work function, such as magnesium-silver alloy, magnesium-indium alloy or aluminum-magnesium alloy.

The organic EL device forming at least one of the organic layers (e.g., electron injection layer 8, electron-transporting layer 7, hole-blocking layer 6 or luminous layer 5) by using the pyrimidine derivative of the present invention, features a high luminous efficiency, a high power efficiency, a low practical driving voltage, a low luminance start voltage and very excellent durability.

Though the invention will now be more concretely described by way of Examples, it should be noted that the invention is in no way limited to these Examples only without, of course, departing from the gist and scope of the invention.

In the following Examples, the glass transition points (Tg) were measured in the powdery form by using a highly sensitive differential scanning calorimeter (DSC 3100SA manufactured by Bruker AXS K.K.).

The work functions were measured in the form of a thin film of a thickness of 100 nm on an ITO substrate by using an ionized potential measuring apparatus (Model PYS-202 manufactured by Sumitomo Heavy Industries, Ltd.)

EXAMPLE 1

Synthesis of a 4-phenyl-2-[3-(10-phenylanthracene-9-il)phenyl]-6-(5-phenyl-5H-pyrido[4,3-b]indole-8-il)pyrimidine (Synthesis of a Compound 1)

(Compound 1)

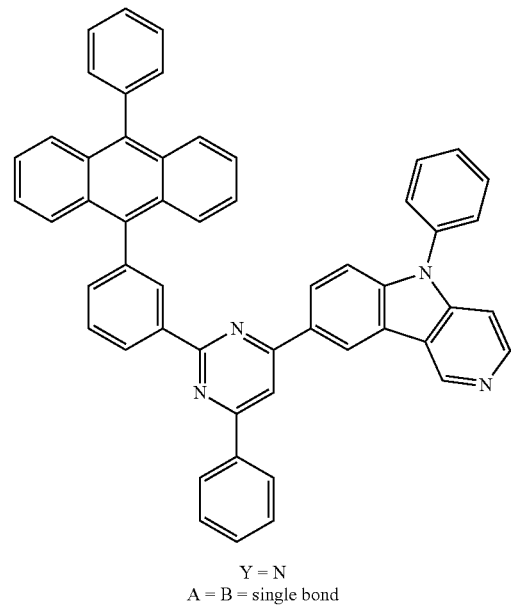

Y = N
A = B = single bond
formula (1a-2)

2-Chloro-4-phenyl-6-(5-phenyl-5H-pyrido[4,3-b]indole-8-il)pyrimidine 4.4 g,
3-(10-phenylanthracene-9-il)phenylboronic acid 4.6 g,
Potassium carbonate 4.2 g,
Tetrakis(triphenylphosphine) palladium 0.35 g,
Toluene 40 ml,
Ethanol 20 ml, and
Water 20 ml,
were put into a reaction vessel purged with nitrogen, were heated and were stirred at 80° C. for 12 hours.

After cooled down to room temperature, methanol was added thereto, and the precipitated crude product was picked up by filtration and washed with water.

Next, the obtained crude product was refined by the column chromatography (carrier: silica gel, eluent: ethyl acetate/n-hexane) and was, thereafter, refined by the recrystallization by using a mixed solvent of toluene/hexane to obtain 5.1 g of a yellow powder of 4-phenyl-2-[3-(10-phenylanthracene-9-il)phenyl]-6-(5-phenyl-5H-pyrido[4,3-b]indole-8-il)pyrimidine (compound 1) (yield, 70%).

The obtained yellow powder was identified for its structure by the NMR. FIG. 1 shows the results of the $^1$H-NMR measurement.

The following 34 signals of hydrogen were detected by the $^1$H-NMR (THF-$d_8$).

δ (ppm)=9.52 (1H)
9.38 (1H)
9.08 (1H)
8.92 (1H)
8.63 (1H)
8.56 (1H)
8.51 (1H)
8.48-8.38 (2H)
7.90-7.78 (3H)
7.78-7.46 (17H)
7.40-7.28 (5H)

EXAMPLE 2

Synthesis of a 4-(phenanthrene-9-il)-2-[3-{10-(5-phenyl-5H-pyrido[4,3-b]indole-8-il)anthracene-9-il}phenyl]-6-phenylpyrimidine (Synthesis of a Compound 35)

(Compound 35)

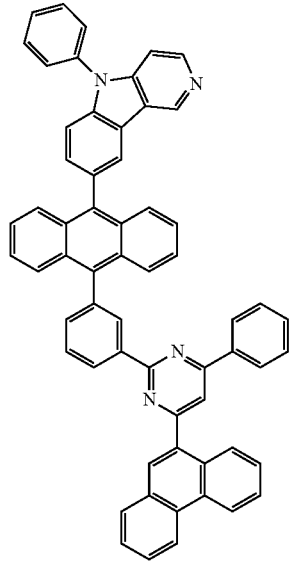

Y = N
formula (1b-2)

4-(Phenanthrene-9-il)-2-{3-(10-bromoanthracene-9-il)phenyl}-6-phenylpyrimidine 10.4 g,
(5-Phenyl-5H-pyrido[4,3-b]indole-8-il)-4,4,5,5-tetramethyl-[1,3,2]dioxaborane 6.7 g,
Potassium carbonate 6.5 g,
Tetrakistriphenylphosphinepalladium 0.54 g,
Toluene 100 ml,
Ethanol 50 ml, and
Water 50 ml,
were put into a reaction vessel purged with nitrogen, and were stirred at 60° C. for 12 hours.

After cooled down to room temperature, the organic layer was picked up by the liquid separation operation. The organic layer was dehydrated with anhydrous magnesium sulfate and was, thereafter, concentrated under reduced pressure to obtain a crude product.

The obtained crude product was refined by the column chromatography (carrier: silica gel, eluent: ethyl acetate/n-hexane) and was, thereafter, refined by the recrystallization by using a mixed solvent of toluene/hexane and, then, by using a mixed solvent of dichloromethane/hexane to obtain 6.3 g of a yellow powder of 4-(phenanthrene-9-il)-2-[3-{10-(5-phenyl-5H-pyrido[4,3-b]indole-8-il)anthracene-9-il}phenyl]-6-phenylpyrimidine (compound 35) (yield, 47%).

Figure 2:
FIG. 2 is a $^1$H-NMR chart of a compound (compound 35) of Example 2.

The obtained yellow powder was identified for its structure by the NMR. FIG. 2 shows the results of the $^1$H-NMR measurement.

The following 38 signals of hydrogen were detected by the $^1$H-NMR (THF-$d_8$).

δ (ppm)=9.37 (1H)
9.00 (1H)
8.95-8.77 (3H)
8.51 (1H)
8.43-8.35 (4H)
8.22 (1H)
8.14 (1H)
8.01 (1H)
7.85-7.56 (17H)
7.54-7.42 (3H)
7.41-7.28 (5H)

EXAMPLE 3

Synthesis of a 2,4-bis(biphenyl-4-il)-6-(5-phenyl-5H-pyrido[4,3-b]indole-8-il)pyrimidine (Synthesis of a Compound 72)

(Compound 72)

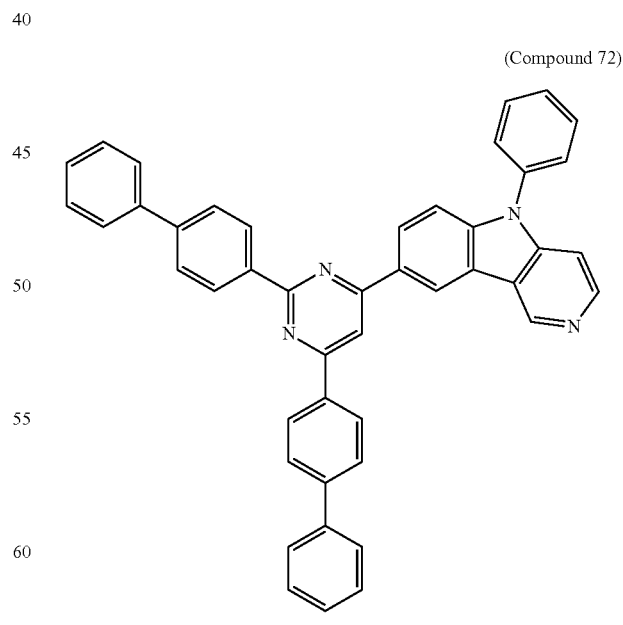

Y = N
A = B = single bond
formula (1a-2)

4-(Biphenyl-4-il)-2-chloro-6-(5-phenyl-5H-pyrido[4,3-b]indole-8-il)pyrimidine 8.2 g,
Biphenyl-4-ilboronic acid 3.8 g,
Potassium carbonate 6.7 g,
Tetrakistriphenylphosphinepalladium 0.93 g,
Toluene 82 ml,
Ethanol 41 ml, and
Water 41 ml,
were put into a reaction vessel purged with nitrogen, were heated and were stirred at 70° C. for 12 hours.

After cooled down to room temperature, heptane was added thereto, and the precipitated crude product was picked up by filtration. The obtained crude product was refined by the crystallization by using a mixed solvent of chlorobenzene/heptane and was refined by the crystallization by using a mixed solvent of methanol/heptane to obtain 4.0 g of a yellow powder of 2,4-bis(biphenyl-4-il)-6-(5-phenyl-5H-pyrido[4,3-b]indole-8-il)pyrimidine (compound 72) (yield, 40%).

Figure 3:
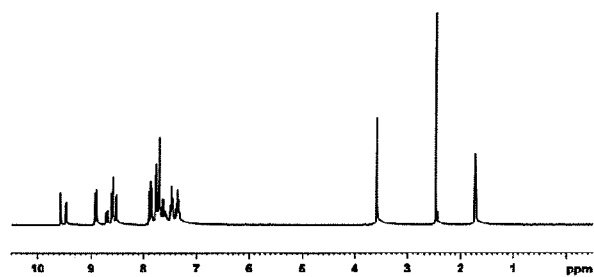
FIG. 3 is a $^1$H-NMR chart of a compound (compound 72) of Example 3.

The obtained yellow powder was identified for its structure by the NMR. FIG. 3 shows the results of the $^1$H-NMR measurement.

The following 30 signals of hydrogen were detected by the $^1$H-NMR (THF-$d_8$).
δ (ppm)=9.58 (1H)
9.46 (1H)
8.92 (2H)
8.70 (1H)
8.62-8.49 (4H)
7.91-7.32 (21H)

EXAMPLE 4

The compounds of the present invention obtained in the above Examples 1 to 3 were measured for their glass transition points. The results were as follows:

|  | Glass transition points |
|---|---|
| Compound of Example 1 | 174° C. |
| Compound of Example 2 | 200° C. |
| Compound of Example 3 | 135° C. |

As described above, the compounds of the present invention have glass transition points which are not lower than 100° C., especially, not lower than 130° C. indicating that the thin films formed by using the compounds of the invention maintain stability.

EXAMPLE 5

By using the compounds of the invention obtained in the above Examples 1 to 3, films were vapor-deposited in a thickness of 100 nm on an ITO substrate and were measured for their work functions by using an apparatus for measuring ionization potentials. The results were as follows:

|  | Work functions |
|---|---|
| Compound of Example 1 | 6.06 V |
| Compound of Example 2 | 6.13 V |
| Compound of Example 3 | 6.23 V |

As described above, the compounds of the present invention have values larger than a work function of 5.5 eV possessed by general hole-transporting materials such as NPD, TPD and the like, and have large hole-blocking powers.

EXAMPLE 6

An organic EL device of a layer structure shown in FIG. 4 was fabricated by forming an ITO electrode as a transparent anode 2 on a glass substrate 1, and by vapor-depositing, on the ITO electrode (transparent anode 2), a hole injection layer 3, a hole-transporting layer 4, a luminous layer 5, a hole-blocking layer 6, an electron-transporting layer 7, an electron injection layer 8 and a cathode (aluminum electrode) 9 in this order.

Concretely, the glass substrate 1 having the ITO electrode (transparent anode 2) of a thickness of 150 nm formed on the surface thereof was washed with ultrasonic waves in an isopropyl alcohol for 20 minutes and was, thereafter, dried on a hot plate heated at 200° C. for 10 minutes.

Thereafter, the glass substrate with ITO was subjected to the UV-ozone treatment for 15 minutes and placed in a vacuum evaporation machine. The pressure therein was reduced down to 0.001 Pa or lower. Next, as the hole injection layer 3, a compound HIM-1 of the following structural formula was formed in a thickness of 5 nm so as to cover the transparent anode 2.

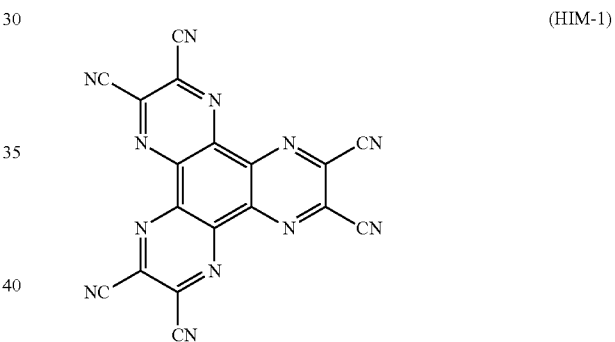

(HIM-1)

The hole-transporting layer 4 was formed on the hole injection layer 3 by depositing a compound HTM-1 of the following structural formula in a thickness of 65 nm.

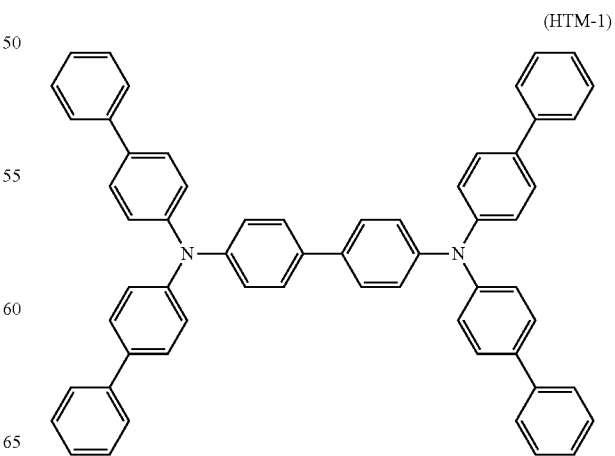

(HTM-1)

On the hole-transporting layer 4, the luminous layer 5 was formed in a thickness of 20 nm by two-way-depositing a compound EMD-1 (NUBD 370 manufactured by SFC Co., Ltd.) and a compound EMH-1 (ABH 113 manufactured by SFC Co., Ltd.) at a deposition rate of EMD-1:EMH-1=5:95.

On the luminous layer 5 formed above, the hole-blocking layer/electron-transporting layer (6, 7) were formed in a thickness of 30 nm by two-way-depositing the compound of the present invention (compound 1) synthesized in Example 1 and a compound ETM-1 of the following structural formula at a deposition rate of compound of Example 1 of the invention (compound 1):ETM-1=50:50.

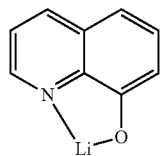

(ETM-1)

On the hole-blocking layer/electron-transporting layer (6, 7), there was formed a film of lithium fluoride in a thickness of 1 nm to thereby form the electron injection layer 8.

Finally, aluminum was deposited in a thickness of 100 nm to form the cathode 9.

The EL device fabricated above was measured for its properties in the atmosphere at normal temperature. Table 1 collectively shows the measured results of luminous characteristics of when a DC voltage was applied to the organic EL device.

The life of the device was measured as the time of from when it initially exhibited a luminance (initial brightness) of 2000 cd/m$^2$ being driven with a constant current until when its luminance decreased down to 1900 cd/m$^2$ (corresponds to 95% relative to the initial luminance of 100%: reduction down to 95%).

EXAMPLE 7

An organic EL device was fabricated in the same manner as in Example 6 but forming the hole-blocking layer/electron-transporting layer (6, 7) by two-way-depositing the compound (compound 72) synthesized in Example 3 and the compound ETM-1 of the above structural formula at a deposition rate of (compound 72):ETM-1=50:50.

The EL device fabricated above was measured for its properties in the atmosphere at normal temperature. Table 1 collectively shows the measured results of luminous characteristics of when a DC voltage was applied to the fabricated organic EL device.

COMPARATIVE EXAMPLE 1

An organic EL device was fabricated in the same manner as in Example 6 but forming the hole-blocking layer/electron-transporting layer (6, 7) by two-way-depositing a compound ETM-2 of the following structural formula (see, e.g., patent document 4) and the compound ETM-1 of the above structural formula at a deposition rate of ETM-2:ETM-1=50:50.

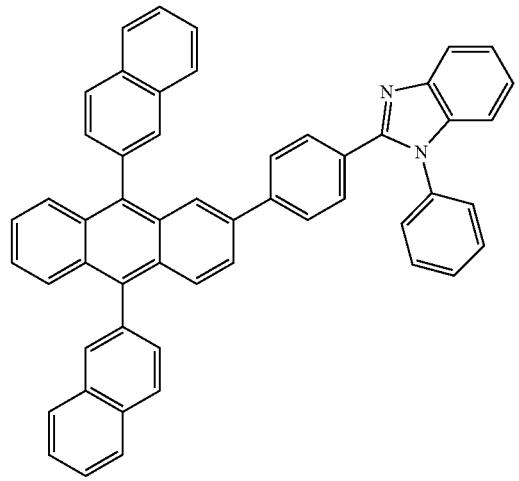

(ETM-2)

The EL device fabricated above was measured for its properties in the atmosphere at normal temperature. Table 1 collectively shows the measured results of luminous characteristics of when a DC voltage was applied to the fabricated organic EL device.

EXAMPLE 8

An organic EL device was fabricated in the same manner as in Example 6 but forming the hole-transporting layer 4 using a compound HTM-2 of the following structural formula and, further, forming the luminous layer 5 by two-way-depositing a compound EMD-2 (SBD 160 manufactured by SFC Co., Ltd.) and a compound EMH-2 (ABH 401 manufactured by SFC Co., Ltd.) as the material of the luminous layer 5 at a deposition rate of EMD-2:EMH-2=5:95.

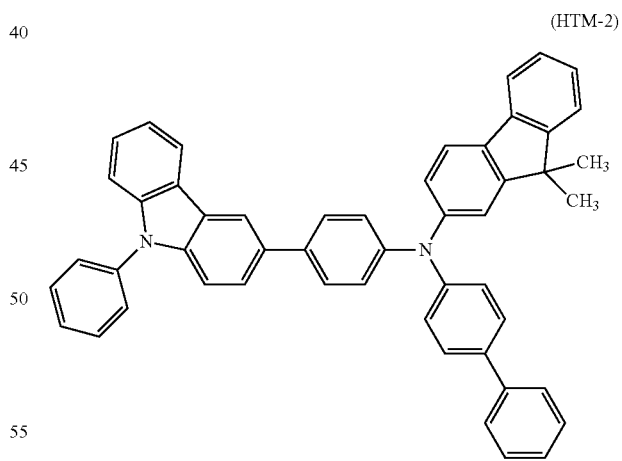

(HTM-2)

The EL device fabricated above was measured for its properties in the atmosphere at normal temperature. Table 1 collectively shows the measured results of luminous characteristics of when a DC voltage was applied to the fabricated organic EL device.

EXAMPLE 9

An organic EL device was fabricated in the same manner as in Example 8 but forming the hole-blocking layer/electron-transporting layer (6, 7) by two-way-depositing the compound (compound 72) of Example 3 and the compound ETM-1 of the above structural formula at a deposition rate of (compound 72):ETM-1=50:50.

The EL device fabricated above was measured for its properties in the atmosphere at normal temperature. Table 1 collectively shows the measured results of luminous characteristics of when a DC voltage was applied to the fabricated organic EL device.

COMPARATIVE EXAMPLE 2

An organic EL device was fabricated in the same manner as in Example 8 but forming the hole-blocking layer/electron-transporting layer (6, 7) by two-way-depositing the compound ETM-2 of the above structural formula and the compound ETM-1 of the above structural formula at a deposition rate of ETM-2:ETM-1=50:50.

The EL device fabricated above was measured for its properties in the atmosphere at normal temperature. Table 1 collectively shows the measured results of luminous characteristics of when a DC voltage was applied to the fabricated organic EL device.

Even in the comparison of Example 8 with Comparative Example 2, Example 8 has a driving voltage of 3.66 V and Example 9 has a driving voltage of 3.67 V which are lower than a driving voltage of 3.79 V of Comparative Example 2. As for the luminous efficiency, Example 8 has a value of 11.21 cd/A and Example 9 has a value of 10.32 cd/A which are greatly increasing as compared to a value of 7.56 cd/A of Comparative Example 2. As for the power efficiency, too, Example 8 has a value of 9.62 lm/W and Example 9 has a value of 8.84 lm/W which are greatly increasing as compared to a value of 6.27 lm/W of Comparative Example 2. Moreover, as for the device life (until decreased down to 95%), Example 8 has 107 hours and Example 9 has 101 hours which are greatly increasing as compared to 75 hours of Comparative Example 2.

As described above, as compared to the devices that use the compound ETM-2 of the above structural formula that is a generally used electron-transporting material, the organic EL device having the organic layer formed by using the pyrmidine derivative of the present invention features excellent luminous efficiency and power efficiency and, further,

TABLE 1

| | Hole-transporting layer | Luminous layer | Hole blocking/ electron transporting layer | *1 | *2 | *3 | *4 | Device life down to 95% |
|---|---|---|---|---|---|---|---|---|
| Ex. 6 | HTM-1 | EMD-1/EMH-1 | compound 1/ETM-1 | 3.73 | 667 | 6.67 | 5.62 | 77 hrs. |
| Ex. 7 | HTM-1 | EMD-1/EMH-1 | compond 72/ETM-1 | 3.66 | 685 | 6.85 | 5.89 | 63 hrs. |
| Comp. Ex. 1 | HTM-1 | EMD-1/EMH-1 | ETM-2/ETM-1 | 3.84 | 635 | 6.35 | 5.20 | 55 hrs. |
| Ex. 8 | HTM-2 | EMD-2/EMH-2 | compound 1/ETM-1 | 3.66 | 1121 | 11.2 | 9.62 | 107 hrs. |
| Ex. 9 | HTM-2 | EMD-2/EMH-2 | compound 72/ETM-1 | 3.67 | 1030 | 10.3 | 8.84 | 101 hrs. |
| Comp. Ex. 2 | HTM-2 | EMD-2/EMH-2 | ETM-2/ETM-1 | 3.79 | 756 | 7.56 | 6.27 | 75 hrs. |

*1: Voltage [V] (@ 10 mA/cm2)
*2: Brightness [cd/m2] (@ 10 mA/cm2)
*3: Luminous efficiency [cd/A] (@ 10 mA/cm2)
*4: Power efficiency [lm/W] (@ 10 mA/cm2)

When an electric current is flown at a current density of 10 mA/cm$^2$ as shown in Table 1, the organic EL device of Comparative Example 1 that uses the compound ETM-2 of the above structural formula drives at a voltage of 3.84 V. On the other hand, the organic EL device of Example 6 that uses the compound (compound 1) of Example 1 drives at a voltage of 3.73 V and the organic EL device of Example 7 that uses the compound (compound 72) of Example 3 drives at a voltage of 3.66 V both of which being lower than the driving voltage of the organic EL device of Comparative Example 1.

As for the luminous efficiency, Example 6 has a value of 6.67 cd/A and Example 7 has a value of 6.85 cd/A which are greatly increasing as compared to the value of 6.35 cd/A of Comparative Example 1. As for the power efficiency, too, Example 6 has a value of 5.62 lm/W and Example 7 has a value of 5.89 lm/W which are greatly increasing as compared to the value of 5.20 lm/W of Comparative Example 1.

As for the device life (until decreased down to 95%), the organic EL device of Example 6 has 77 hours and the organic EL device of Example 7 has 63 hours which are greatly increasing as compared to 55 hours of the organic EL device of Comparative Example 1.

realizes an extended life. Moreover, the practical driving voltage can be conspicuously lowered.

INDUSTRIAL APPLICABILITY

The pyrimidine derivative of the present invention has good electron injection property and excellent hole-blocking power, remains stable in its thin film state, and can be favorably used as a compound for fabricating the organic EL devices. Upon fabricating the organic EL devices by using the above compound, it is allowed to attain a high efficiency, to lower the driving voltage and to improve the durability. Its use can, therefore, be expanded to, for example, domestic appliances and illumination equipment.

DESCRIPTION OF SYMBOLS 1 glass substrate
2 transparent anode
3 hole injection layer
4 hole-transporting layer
5 luminous layer
6 hole-blocking layer 7 electron-transporting layer
8 electron injection layer
9 cathode

The invention claimed is:

1. Pyrimidine derivatives selected from the group consisting of compounds represented by the following structural formulae:

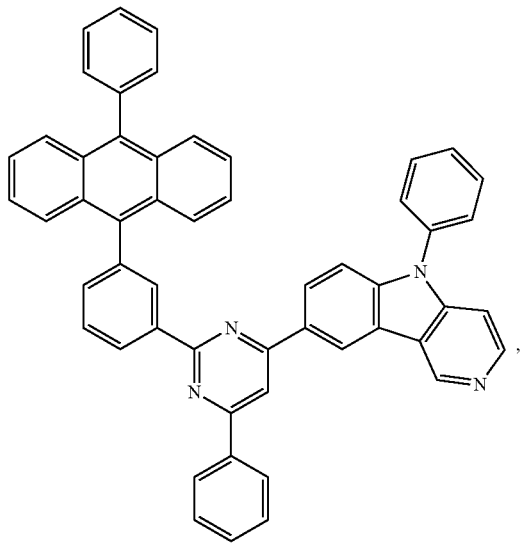

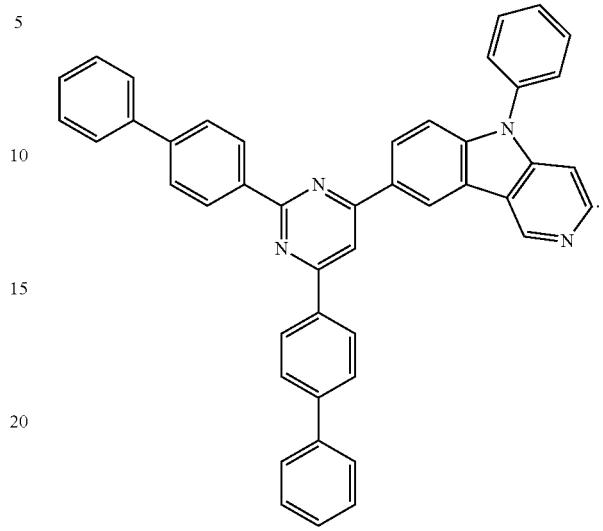

2. Pyrimidine derivatives according to claim 1, wherein the pyrimidine derivatives are elected from the group consisting of compounds represented by the following structural formulae:

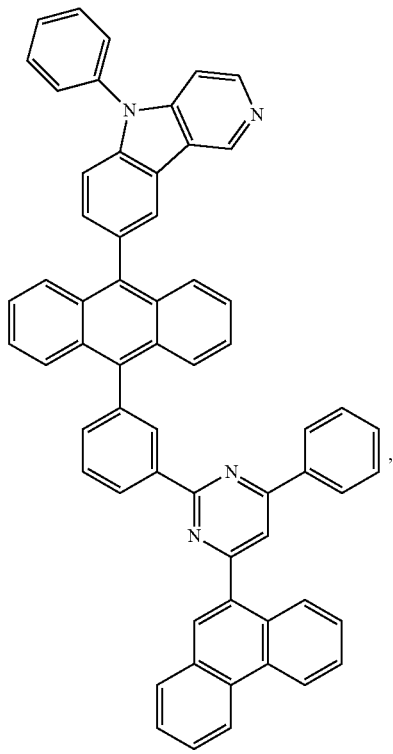

and

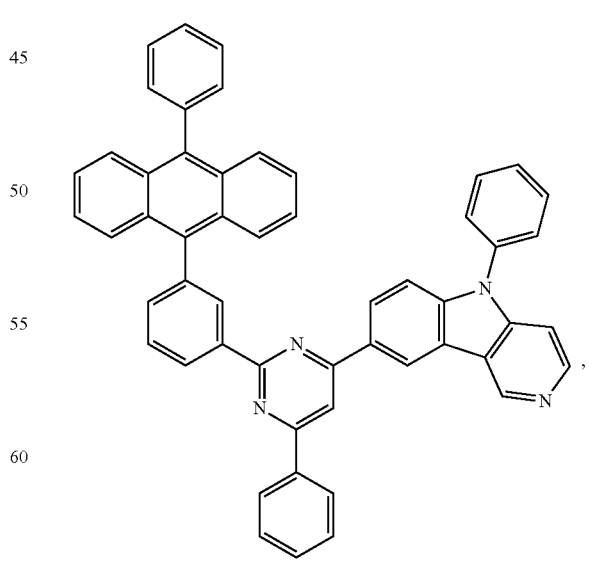

and

-continued

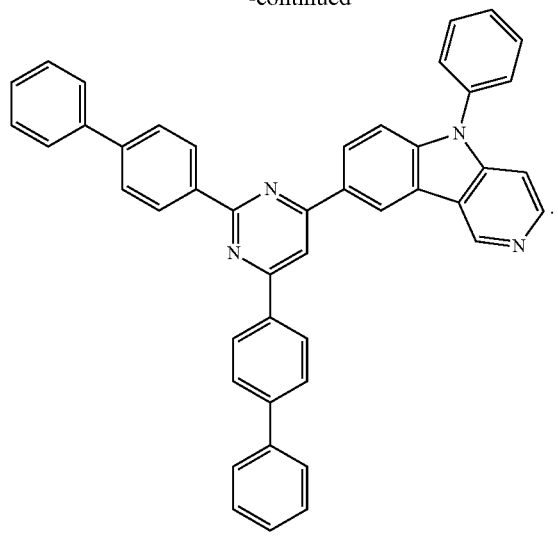

3. An organic electroluminescent device having a pair of electrodes and at least one organic layer held therebetween, wherein the pyrimidine derivative of claim 1 is used as the material for constituting at least one organic layer.

4. The organic electroluminescent device according to claim 3, wherein the organic layer is the electron-transporting layer.

5. The organic electroluminescent device according to claim 3, wherein the organic layer is the hole-blocking layer.

6. The organic electroluminescent device according to claim 3, wherein the organic layer is the luminous layer.

7. The organic electroluminescent device according to claim 3, wherein the organic layer is the electron injection layer.

* * * * *